US011516625B2

(12) United States Patent
Lagace et al.

(10) Patent No.: US 11,516,625 B2
(45) Date of Patent: Nov. 29, 2022

(54) SYSTEMS AND METHODS FOR MAPPING A GIVEN ENVIRONMENT

(71) Applicant: MOONSHOT HEALTH INC., Montreal (CA)

(72) Inventors: Etienne Lagace, Montreal (CA); Remy Beaumont, Saint-Augustin-de-Desmaures (CA)

(73) Assignee: MOONSHOT HEALTH INC., Montreal (CA)

( * ) Notice: Subject to any disclaimer, the term of this patent is extended or adjusted under 35 U.S.C. 154(b) by 0 days.

(21) Appl. No.: 17/268,557

(22) PCT Filed: Aug. 19, 2019

(86) PCT No.: PCT/CA2019/051123
§ 371 (c)(1),
(2) Date: Feb. 15, 2021

(87) PCT Pub. No.: WO2020/037399
PCT Pub. Date: Feb. 27, 2020

(65) Prior Publication Data
US 2021/0321222 A1  Oct. 14, 2021

Related U.S. Application Data

(60) Provisional application No. 62/720,663, filed on Aug. 21, 2018.

(51) Int. Cl.
*H04W 4/029* (2018.01)
*H04W 4/021* (2018.01)
(52) U.S. Cl.
CPC ........... *H04W 4/029* (2018.02); *H04W 4/021* (2013.01)

(58) Field of Classification Search
CPC ....... H04W 4/029; H04W 4/021; H04W 4/02; H04W 4/30; H04W 4/33; H04W 4/35;
(Continued)

(56) References Cited

U.S. PATENT DOCUMENTS 8,068,051 B1    11/2011  Osterweil
2013/0141233 A1*  6/2013  Jacobs et al. .......... G08B 19/00
(Continued)

FOREIGN PATENT DOCUMENTS

CN    104819716 A  *  8/2015
EP    2209018 A1    7/2010
(Continued)

OTHER PUBLICATIONS

International Search Report and Written Opinion issued in parent application No. PCT/CA2019/051123 dated Nov. 13, 2019.
(Continued)

*Primary Examiner* — Meless N Zewdu
(74) *Attorney, Agent, or Firm* — BCF LLP

(57) ABSTRACT

Methods and systems for mapping boundaries of a given environment by a processor of a computer system, the method comprising: determining a trajectory of the body in the given environment over the given time period; and determining, based on the trajectory of the body in the given environment, one or more of an outer boundary of the given environment, and an inner boundary of the given environment. Methods and systems for mapping functionalities of a given environment executable by a processor of a computer system, the method comprising determining a pattern of movement of a body in the given environment in a given time period; and determining a functional identity of at least
(Continued)

one zone in the given environment based on the pattern of movement of the body to obtain a mapped given environment.

20 Claims, 9 Drawing Sheets

(58) Field of Classification Search
CPC .......... H04W 4/38; H04W 4/50; H04W 4/60; H04W 4/80; H04W 4/90; H04W 68/00; H04W 68/04; H04W 64/00; H04W 64/003; H04W 64/006; H04W 84/18; H04W 60/04; H04W 12/64; H04W 12/79; H04W 12/65; H04W 12/68; H04W 12/63; H04W 12/42; H04W 12/104; H04W 12/009; H04W 4/027; H04W 4/026; G01S 13/0209; G01S 13/582; G01S 13/584; G01S 7/412; G01S 7/415; G01S 7/417; G01S 13/04; G01S 13/46; G01S 13/56; G01S 13/72; G01S 2013/466; G01S 2013/468; G01S 13/89; G01S 13/586; G01S 2201/01; G01S 2201/02; G01S 2201/025; G01S 2201/07; G01S 2205/02; G01S 13/862; G01S 5/014; G01S 13/88; G01S 13/48; G01S 5/015; G01S 5/013; G01S 5/012; G01S 5/016; G01S 5/00; G08B 21/043; G08B 21/0469; G08B 21/22; G06N 20/00; G01D 21/00; A61B 5/02055; A61B 5/1113; A61B 5/1117; A61B 2505/07

See application file for complete search history.

(56) References Cited

U.S. PATENT DOCUMENTS

| | | | |
|---|---|---|---|
| 2017/0357264 A1 | 12/2017 | Watanabe et al. | |
| 2018/0143024 A1* | 5/2018 | Kay et al. | ............ G01C 21/206 |

FOREIGN PATENT DOCUMENTS

| | | | | |
|---|---|---|---|---|
| EP | 3287808 A1 * | 2/2018 | ............. | G01S 11/04 |
| WO | 0101168 A2 | 1/2001 | | |
| WO | 2009021068 A1 | 2/2009 | | |
| WO | WO 2013132393 A * | 9/2013 | ............... | G01S 5/30 |
| WO | WO 2014071860 A1 * | 5/2014 | ............... | G06K 7/00 |
| WO | 2016193972 A2 | 12/2016 | | |

OTHER PUBLICATIONS

Supplementary European Search Report issued in corresponding European application No. 19851138.8 dated May 9, 2022.

* cited by examiner

SYSTEMS AND METHODS FOR MAPPING A GIVEN ENVIRONMENT

CROSS-REFERENCE TO RELATED APPLICATIONS

The present application is a National Stage of International Application No. PCT/CA2019/051123, filed on Aug. 19, 2019, which claims priority to U.S. Provisional Application No. 62/720,663, filed Aug. 21, 2018, and entitled "Systems and Methods for Mapping a Given Environment." The entire contents of each application listed in this paragraph are incorporated herein by reference.

FIELD

The present technology relates to systems and methods for mapping a given environment.

BACKGROUND

There are many circumstances in which mapping of a given environment may be useful. One such example is for the purposes of positioning or tracking of a body in the given environment such as in home surveillance, for child monitoring or in care home settings, for example.

Existing positioning technologies include radar systems, GPS systems or RFID tags.

RFID tags, and GPS devices (e.g. wearable sensors) are associated with the body being tracked and therefore allow the positioning of the body in that manner (see for example EP3196854). However, these suffer from the inconvenience of necessitating the body being tracked to carry the tracking device. They are essentially rendered useless if the tracking device is not on the body being tracked.

Radar systems, such as those used in home surveillance, can detect an approximate distance of an object in a three-dimensional space by transmitting signals and detecting the reflected transmitted signals from the object. The transmitted and detected signals can be electromagnetic signals, such as signals within the radio frequency bandwidth. For an exact position of the body, triangulation is needed which requires a plurality of units for transmitting and detecting signals.

However, both radar and tagged systems require knowledge of the map of the given environment in order to provide meaningful tracking information.

For example, in a set-up phase, the radar transmitter/detector units must be installed in a set position, and then calibrated to set the zone within which the system will operate (see for example WO2015102713 and U.S. Pat. No. 9,753,131). This is especially important in settings including a number of separate dwelling units with shared walls or in close proximity to one another such that the definition of the boundaries of the given environment in which the body tracking is required is important.

Therefore, there is a need for systems and methods for determining a body position that overcomes at least some of the above-identified drawbacks.

SUMMARY

Embodiments of the present technology have been developed based on developers' appreciation of shortcomings associated with the prior art.

In particular, such shortcomings may comprise (1) the necessity for a manual set-up phase to establish the boundaries and/or zones of the given environment in which tracking is required; and (2) limited information available through body tracking using existing systems, such as using information from only a single sensor located at one position.

Broadly, developers have identified that, in certain aspects and embodiments of the present technology, a given environment can be mapped using information regarding a body's localization habits within that given environment, or using a body's trajectory (path) of movement in the given environment. This mapped given environment can be used to track a body, or identify events such as falls, changes in condition, likelihood of location, etc. The body can be that of a person, an animal or a robot. In certain embodiments, by localization habits is meant patterns of movement such as one or more of: time spent in a certain location, frequency of being located at certain locations; time(s) of day at the location, sequence of being located at certain locations, speed of movement within the given environment, a transition time between one or more locations, number of transitions between locations, or the like. Body positions may or may not be included within the localization habit, such as standing, lying, sitting. By the body's trajectory of movement in the given environment is meant one or more paths of movement of the body within the given environment. The trajectory can be two-dimensional or three-dimensional or a combination of both two- and three-dimensional.

In certain embodiments, by mapping the given environment is meant defining one or more of (i) one or more outer boundaries of the given environment, (ii) one or more inner boundaries of the given environment, (ii) one or more rooms/zones within the given environment, which could be defined by a functionality of the rooms/zones, and (iii) the relative position or layout of the rooms/zones within the given environment (e.g. bedroom is in North West region of the given environment), and the like.

By means of certain embodiments, the requirement of a manual set-up to define the given environment in which the body tracking is required is alleviated. By defining the given environment is meant defining any one or more of the inner or outer boundaries, defining one or more zones, defining a layout of the given environment. In certain embodiments, this can provide a "drop-and-play" system which is easy to use and requires none or minimal configuration.

In certain embodiments, the present technology can be used to map given environments for the purposes of tracking or monitoring people in their homes, residential homes, hospitals, prisons, rehabilitation centres, work etc. Through such tracking or monitoring, deviations from an average or a threshold can be detected and an appropriate action taken such as raising an alarm. Such tracking or monitoring in view of certain biomarkers can also provide certain health or condition indications.

In certain embodiments, the present technology can also be used to assist first responders. Provision of an indication of a location of a bedroom to a firefighter, for example, can facilitate their rescue efforts by directing them.

The given environment can be an indoor space, an outdoor space or a combination of indoor and outdoor spaces. For example, in one given environment, the given environment is a home having some outside space associated with it (e.g. balcony, garden, terrace, etc).

From one broad aspect, the method and system of mapping the given environment comprises comparing a pattern of movement of a body in the given environment (localization habits) with information from databases of daily living (reference pattern of movement). Such daily living databases provide data about average time or frequency (minutes or hours) per day spent on specific activities. The activity being performed may be identified based on radar baseband readings, Doppler information, recorded sounds, vibration measurements, and/or other measured data. The daily living databases are categorized in terms of factors that may affect the daily living habit of a person. At least some of these factors include: biological factors (e.g., age, gender, weight, medical condition, medication, etc.), demographic factors (e.g. ethnicity, cultural background, demographic classification, wealth etc.), geolocation factors (e.g., poor neighbourhood, rich neighbourhood, apartment block, bungalow, southern/northern hemisphere), and contextual factors (e.g. season, weather, temperature, day light hours etc.). In certain embodiments, this daily living information is augmented with data regarding where these activities are likely to take place (e.g. room or region), and how much time is spent on average per room (e.g. according to the various factors such as age group, gender, etc.).

From one aspect, there is provided a method for mapping a given environment, the method executable by a processor of a computer system, the method comprising: determining a pattern of movement of a body in the given environment in a given time period; and determining a functional identity of at least one zone in the given environment based on the pattern of movement of the body in the given environment to obtain the mapping of the given environment.

In certain embodiments, the functional identity of the at least one zone is selected from a: living zone, sleeping zone, a resting zone, a cooking zone, an eating zone, a recreational zone, a bathroom zone, a hallway zone, a doorway zone, and the like.

In certain embodiments, the pattern of movement is an average pattern of movement based on a plurality of patterns of movement of the body determined in a plurality of different time slots or periods.

In certain embodiments, the pattern of movement is defined by a sequence of co-ordinates or location vectors of the location of the body as a function of time.

In certain embodiments, the determining the identity of the at least one zone in the given environment comprises grouping together certain of the co-ordinates or location vectors based on a commonality or similarity of the co-ordinates or location vectors in terms of at least one of: (i) a physical proximity of the co-ordinates or location vectors to one another, (ii) a duration of time spent at certain of the co-ordinates or location vectors by the body in a predetermined time interval, (iii) a time(s) of day of location of the body at certain co-ordinates or location vectors in the predetermined time interval, (iv) a sequence of location of the body at certain co-ordinates or location vectors in the predetermined time interval, (v) a frequency of location of the body at certain co-ordinates or location vectors in the predetermined time interval, (vi) contextual data about the given environment, (vii) geolocation data of the given environment, (viii) activities performed within the zone, and the like. For example, if a body is determined to be taking a shower in a zone, such as by detecting an increase in noise, humidity, and temperature in the zone, the zone may be labelled as a bathroom.

In certain embodiments, the method further comprises comparing the pattern of movement with a reference pattern of movement of a reference body in a reference given environment.

In certain embodiments, the reference pattern of movement is selected based on a relevance of one or more of the following factors to the body and/or to the given environment: biological factors relating to the body (e.g., age, gender, weight, medical condition, medication, DNA, biomarker, other medical considerations as may be contained in a body's medical record etc.), demographic factors relating to the body (e.g. ethnicity, cultural background, demographic classification, wealth etc.), geolocation factors relating to the given environment (e.g., poor neighbourhood, rich neighbourhood, apartment block, bungalow, southern/northern hemisphere), and contextual factors relating to the given environment (e.g. time of year, season, weather, temperature, daylight hours etc.).

In certain embodiments, the reference pattern of movement is selected based on a relevance of one or more of (i) an age/gender of the body compared to the reference body, (ii) a condition/diagnosis/state of the body compared to a condition/diagnosis of the reference body, (iii) a time of year that the pattern of movement is determined compared to a time of year that the reference pattern of movement was determined, (iv) a geolocation of the body compared to a geolocation of the reference body, (v) a specified event of the body compared to a specified event of the reference body, (vi) environmental conditions associated with the body compared to reference environmental conditions, (vii) gender of the body compared to a gender of the reference body, (viii) cultural background of the body compared to a cultural background of the reference body, (ix) DNA mapping of the body compared to DNA mapping of the reference body, (x) biomarker of the body compared to a biomarker of the reference body, and (xi) medication being taken by the body compared to a medication taken by the reference body.

In certain embodiments, the reference pattern of movement defines one or more of: (i) a time spent in one or more zones of the reference environment, (ii) a time of day spent in one or more zones of the reference environment, (iii) a sequence of being located in one or more zones of the reference environment, (iv) a frequency of being located in one or more zones of the reference environment, (v) a speed of movement within the reference environment, (vi) a transition time between one or more zones of the reference environment, (vii) number of transitions between zones of the reference environment, and (viii) activities and/or types of activities performed in one or more zones of the reference environment.

In certain embodiments, the method further comprises obtaining physiological data about the body at the time of determining the pattern of movement.

In certain embodiments, the method further comprises obtaining contextual data about the given environment at the time of determining the pattern of movement. The contextual data may comprise one or more of sound data, vibration data, magnetic data, electromagnetic radiation, air quality data, air humidity data, temperature data, air pressure data, oxygen levels, carbon dioxide levels, luminosity levels, UV levels, time of day, time of week, time of month, season, geolocation and weather conditions.

In certain embodiments, the method further comprises determining the location of inanimate objects in the given environment.

In certain embodiments, the determining the identity of the at least one zone in the given environment comprises the computer system executing a Machine Learning Algorithm (MLA), such as an MLA configured to identify activities being performed in the zone. In certain embodiments, wherein, prior to the obtaining the pattern of movement, the method further comprises executing a training process for the MLA.

In certain embodiments, the training process comprises providing at least one training set, the training set including patterns of movement of reference bodies in reference environments, and a target value representative of a functional identity of a zone; the reference patterns of movement of the reference bodies including various factors, as described above, relating to the body or to the given environment which may affect the patterns of movement. These factors may include biological factors relating to the body, a health status relating to the body, demographic factors relating to the body, geolocation factors relating to the body/given environment, and contextual factors relating to the body/given environment.

In certain embodiments, the reference patterns of movement of the reference bodies include at least one of: an age/gender of the reference bodies, a condition/diagnosis/state of the reference bodies, a time of year that the reference pattern of movement is determined, a time of day that the reference pattern of movement is determined, a time of week that the reference pattern of movement is determined, a geolocation of the reference bodies, specified event(s) of the reference bodies, time spent in one or more zones of the reference environments, time of day spent in one or more zones of the reference environment, a sequence of being located in one or more zones of the reference environment, a frequency of being located in one or more zones of the environment, and contextual parameters about the reference environment.

In certain embodiments, the determining the pattern of movement of the body comprises processing detected radio frequency signals to identify locations of the body in the given environment as a function of time.

In certain embodiments, the determining an identity of at least one zone comprises identifying, based on at least one detected radio frequency signal, any one or more of (i) inanimate objects in the given environment, (ii) an outer boundary of the given environment, (iii) an inner boundary of the given environment, and (iv) types of activities performed in the at least one zone.

In certain embodiments, the method further comprises transmitting radio frequency signals, and detecting the reflected radio frequency signals using a mapping device in the given environment, the mapping device being in communication with the processor, and optionally the mapping device being stationary.

In certain embodiments, the method further comprises validating the determined identity of the at least one zone based on a user input, and optionally further comprising providing a prompt to the user before obtaining the user input.

In certain embodiments, the method further comprises establishing a baseline pattern of movement for the body in the given environment. The method may further comprise detecting a change in the baseline pattern of movement for the body in the given environment.

In certain embodiments, the method further comprises triggering an alert if the change from the baseline pattern of movement is outside of a predetermined threshold.

In certain embodiments, the method further comprises triggering an alert if a predetermined event and/or activity is detected.

In certain embodiments, the method further comprises adjusting the baseline pattern of movement based on an external factor associated with the body, optionally the external factor being one or more selected from medication, a current treatment, a time lapse since a past treatment (e.g. post-operative).

In certain embodiments, the method further comprises determining one or more of an outer boundary of the given environment, and an inner boundary of the given environment.

In certain embodiments, the determining the outer boundary of the given environment comprises identifying outermost points of a trajectory of the body in the given environment. In certain embodiments, determining the inner boundary of the given environment comprises segmenting a trajectory of the body in the given environment into zones of movement, and approximating a boundary in between the zones.

In certain embodiments, segmenting the trajectory into zones comprises grouping together a plurality of co-ordinates or location vectors of the trajectory of the body based on one or more of: (i) a physical proximity of the co-ordinates or location vectors to one another, (ii) a duration of time spent at certain of the co-ordinates or location vectors by the body in a predetermined time interval, (iii) a time(s) of day of location of the body at certain co-ordinates or location vectors in the predetermined time interval, (iv) a sequence of location of the body at certain co-ordinates or location vectors in the predetermined time interval, (v) a frequency of location of the body at certain co-ordinates or location vectors in the predetermined time interval, (vi) contextual data about the given environment, and geolocation data of the given environment.

In certain embodiments, the determining the one or more of an outer boundary of the given environment, and an inner boundary of the given environment comprises the computer system executing a Machine Learning Algorithm (MLA).

In certain embodiments, prior to determining the one or more of an outer boundary of the given environment, and an inner boundary of the given environment, the method further comprises executing a training process for the MLA.

In certain embodiments, the training process comprises providing at least one training set, the training set including a reference trajectories of movement of reference bodies in given environments with outer and inner boundaries, and a target value representative of a location of one or more of an outer boundary and an inner boundary; the reference trajectories of movement optionally including at least one factor, as described above, relating to the body or to the given environment which may affect the trajectories of movement. These factors may include biological factors relating to the body, a health status relating to the body, demographic factors relating to the body, geolocation factors relating to the body/given environment, and contextual factors relating to the body/given environment.

In certain embodiments, the reference trajectories of movement optionally including at least one of an age/gender of the reference bodies, a condition/diagnosis/state of the reference bodies, a time of year that the reference pattern of movement is determined, a time of day that the reference pattern of movement is determined, a time of week that the reference pattern of movement is determined, a geolocation of the reference bodies, specified event(s) of the reference bodies, time spent in one or more zones of the reference environments, time of day spent in one or more zones of the reference environment, a sequence of being located in one or more zones of the reference environment, a frequency of being located in one or more zones of the environment, and contextual parameters about the reference environment.

From another aspect there is provided a system for mapping a given environment, the system comprising a computer system operatively coupled or coupleable to a mapping device, the computer system having a processor arranged to execute a method as defined herein. In certain embodiments, the method comprises: determining a pattern of movement of the body as a function of time; and determining an identity of at least one zone in the given environment based on the pattern of movement of the body, such as the path that the body has traveled throughout the environment and/or the motions of the body while performing an activity, to obtain a mapped given environment.

In certain embodiments, the mapping device is configured to transmit and emit radio frequency signals, and may include a radio frequency transmitter and receiver. The mapping device may receive instructions from the computer system to transmit and receive radio frequency signals. The mapping device may be configured to transmit radio frequency signals to the computer system. In certain embodiments, the mapping device may have two or three units. In certain embodiments, the system or the mapping device further comprises one or more sensors for obtaining contextual data or physiological data. In certain embodiments, one or more of the mapping device, the sensors, and the computer system are integral. The mapping device and/or at least one of the units may comprise a base and a cover defining a hollow body. One or more of the transmitter, the receiver, and the sensors may be contained within the hollow body.

From another aspect, there is provided a method for mapping boundaries of a given environment, the method executable by a processor of a computer system, the method comprising: determining, a trajectory of a body in a given environment over a given time period; determining, based on the trajectory of the body in the given environment, one or more of an outer boundary of the given environment, and an inner boundary of the given environment. In certain embodiments, the determining the trajectory comprises determining a path of movement of the body using emitted and received radio frequency signals.

In certain embodiments, the method further comprises emitting and receiving radio frequency signals in the given environment over a given time period, the received radio frequency signals including radio frequency signals reflected from a body moving in the given environment. The received radio frequency signals may be received from at least one mapping device.

In certain embodiments, determining the outer boundary comprises identifying outermost points of the trajectory.

In certain embodiments, determining the inner boundary of the given environment comprises segmenting the trajectory into zones of movement, and approximating a boundary in between the zones.

In certain embodiments, the segmenting the trajectory into zones comprises grouping a plurality of co-ordinates or location vectors of the trajectory of the body based on one or more of: (i) a physical proximity of the co-ordinates or location vectors to one another, (ii) a duration of time spent at certain of the co-ordinates or location vectors by the body in the given time period, (iii) a time(s) of day of location of the body at certain co-ordinates or location vectors in the given time period, (iv) a sequence of location of the body at certain co-ordinates or location vectors in the given time period, (v) a frequency of location of the body at certain co-ordinates or location vectors in the given time period, (vi) contextual data relating to the given environment, and (vii) geolocation of the body/given environment.

In certain embodiments, the method further comprises obtaining contextual data about the given environment at the time of determining the trajectory of movement of the body.

In certain embodiments, the contextual data comprises one or more of sound data, vibration data, magnetic data, electromagnetic radiation, air quality data, air humidity data, temperature data, barometric pressure data, oxygen levels, carbon dioxide levels, luminosity levels, UV levels, a time of day, a time of week, a time of year, a season, geolocation and weather conditions.

In certain embodiments, the method further comprises determining the location of inanimate objects in the given environment.

In certain embodiments, the method further comprises obtaining physiological data about the body at the time of determining the pattern of movement.

In certain embodiments, the determining one or more of the outer boundary of the given environment, and the inner boundary of the given environment comprises the computer system executing a Machine Learning Algorithm (MLA).

In certain embodiments, prior to determining the one or more of an outer boundary of the given environment, and an inner boundary of the given environment, the method further comprises executing a training process for the MLA.

In certain embodiments, the training process comprises providing at least one training set, the training set including a reference trajectories of movement of reference bodies in given environments with outer and inner boundaries, and a target value representative of a location of one or more of an outer boundary and an inner boundary; the reference trajectories of movement optionally including at least one of: an age/gender of the reference bodies, a condition/diagnosis/state of the reference bodies, a time of year that the reference pattern of movement is determined, a time of day that the reference pattern of movement is determined, a time of week that the reference pattern of movement is determined, a geolocation of the reference bodies, specified event(s) of the reference bodies, time spent in one or more zones of the reference environments, time of day spent in one or more zones of the reference environment, a sequence of being located in one or more zones of the reference environment, a frequency of being located in one or more zones of the environment, and contextual parameters about the reference environment.

In certain embodiments, the determining the outer boundary of the given environment, and an inner boundary of the given environment further comprises determining a pattern of movement of the body in the given environment in the given time period, and determining a functional identity of at least one zone in the given environment based on the pattern of movement of the body.

In certain embodiments, the functional identity of the at least one zone is one or more selected from a: living zone, sleeping zone, a resting zone, a cooking zone, an eating zone, a recreational zone, a bathroom zone, a hallway zone, a doorway zone.

In certain embodiments, the method further comprises comparing the pattern of movement with a reference pattern of movement of a reference body in a reference environment.

In certain embodiments, the reference pattern of movement is selected based on a relevance of (i) an age/gender of the body compared to the reference body, (ii) a condition/diagnosis of the body compared to a condition/diagnosis of the reference body, (iii) a time of year that the pattern of movement is determined compared to a time of year that the reference pattern of movement was determined, (iv) a geolocation of the body compared to a geolocation of the reference body, or (v) a specified event of the body compared to a specified event of the reference body, (vi) gender of the body compared to a gender of the reference body, (vii) cultural background of the body compared to a cultural background of the reference body, (viii) DNA mapping of the body compared to DNA mapping of the reference body, (ix) biomarker of the body compared to a biomarker of the reference body, (x) medication being taken by the body compared to a medication taken by the reference body, (xi) contextual data about the environment.

In certain embodiments, the reference pattern of movement defines one or more of: (i) a time spent in one or more zones of the reference environment, (ii) a time of day spent in one or more zones of the reference environment, (iii) a sequence of being located in one or more zones of the reference environment, (iv) a frequency of being located in one or more zones of the environment, (v) a speed of movement within the reference environment, (vi) a transition time between one or more zones of the reference environment, and (vii) number of transitions between zones of the reference environment.

In certain embodiments, the determining the identity of the at least one zone in the given environment comprises the computer system executing a Machine Learning Algorithm (MLA).

In certain embodiments, the determining the pattern of movement of the body comprises processing detected radio frequency signals to identify locations of the body in the given environment as a function of time.

In certain embodiments, the method further comprises validating the determined outer boundary or inner boundary based on a user input.

From another aspect, there is provided a system for mapping boundaries of a given environment, the system comprising a computer system operatively coupled or coupleable to a mapping device, the computer system having a processor arranged to execute a method as defined above. In one embodiment, the method comprises receiving radio frequency signals in the given environment, from the mapping device, over a given time period, the received radio frequency signals including radio frequency signals reflected from a body moving in the given environment; determining, from the received radio frequency signals, a trajectory of the body in the given environment over the given time period; determining, based on the trajectory of the body in the given environment, one or more of an outer boundary of the given environment, and an inner boundary of the given environment.

The mapping device may be configured to receive instructions to transmit and/or receive radio frequency signals. The mapping device may also be configured to transmit the received radio frequency signals to the computer system. In certain embodiments, the mapping device has two or more units, optionally three units. In certain embodiments, the system and/or the mapping device further comprises one or more sensors for obtaining contextual data and/or physiological data. The mapping device may also include a power unit capable of providing power to the mapping device or capable of connecting to a power source. In certain embodiments, the power unit is a plug extending from the mapping device, for communication with an electrical socket.

In certain embodiments of any of the systems described above, the mapping device and/or any of the units comprise a radio frequency transmitter and receiver. Optionally the mapping device and/or any of the units comprise one or more sensors such as a microphone, a luminosity meter etc. The mapping device and/or at least one of the units may comprise a base and a cover defining a hollow body. One or more of the transmitter, the receiver, and the sensors may be contained within the hollow body.

From another aspect, there is provided a method for mapping a given environment, the method being executable by a processor of a computer system, and comprising (i) mapping boundaries of the given environment, and (ii) determining zones within the mapped given environment.

For example, in certain embodiments, the method of mapping the given environment comprises (i) determining a trajectory of the body in the given environment over the given time period, (ii) determining, based on the trajectory of the body in the given environment, one or more of an outer boundary of the given environment, and an inner boundary of the given environment, (iii) determining a pattern of movement of the body in the given environment, in which at least one or more of the inner and outer boundaries have been mapped, in a given time period; and (iv) determining a functional identity of at least one zone in the given environment based on the pattern of movement of the body in the given environment to obtain the mapping of the given environment. In certain embodiments, the method further comprises monitoring or tracking the body in the mapped given environment in order to detect a deviation from a baseline pattern of movement or to detect an event such as a fall, etc.

From a yet further aspect, there is provided methods and systems of detecting events, such as falls, wanderings, faucets left on, intruder or the like, the methods and systems being in accordance with any of the above defined aspects and embodiments.

From another aspect, there is provided methods and systems for monitoring a health or well being of a body in a given environment, the methods and systems according to any of the above defined aspects and embodiments.

From a yet further aspect, there is provided a mapping device comprising a base and a cover defining a hollow body. One or more of a radio frequency transmitter, a radio frequency receiver, and at least one sensor, are positioned in the hollow body. The hollow body may also include a processor for processing signals from the radio frequency receiver and/or the at least one sensor. The processor may be external to the mapping device and the mapping device may be configured to transmit the received radio frequency signals to the processor. The processor may also be arranged to carry out, at least partially, any of the methods described above. The mapping device may also include a power unit capable of providing power to the mapping device or connecting to a power source. In certain embodiments, the power unit is a plug extending from the base, for communication with an electrical socket. The cover can be removably attachable to the base. In certain embodiments, the cover includes at least one opening or at least one window, with the at least one sensor positioned adjacent the opening or window. For certain sensor types, this can facilitate signal detection such as in the case of a microphone or a luminosity meter contained within the hollow body.

In the context of the present specification, unless expressly provided otherwise, a computer system may refer, but is not limited to, an "electronic device", an "operation system", a "system", a "computer-based system", a "controller unit", a controller", "a processor", a "control device" and/or any combination thereof appropriate to the relevant task at hand.

In the context of the present specification, unless expressly provided otherwise, the expression "computer-readable medium" and "memory" are intended to include media of any nature and kind whatsoever, non-limiting examples of which include RAM, ROM, disks (CD-ROMs, DVDs, floppy disks, hard disk drives, etc.), USB keys, flash memory cards, solid state-drives, and tape drives. Still in the context of the present specification, "a" computer-readable medium and "the" computer-readable medium should not be construed as being the same computer-readable medium. To the contrary, and whenever appropriate, "a" computer-readable medium and "the" computer-readable medium may also be construed as a first computer-readable medium and a second computer-readable medium.

In the context of the present specification, unless expressly provided otherwise, the words "first", "second", "third", etc. have been used as adjectives only for the purpose of allowing for distinction between the nouns that they modify from one another, and not for the purpose of describing any particular relationship between those nouns.

Implementations of the present technology each have at least one of the above-mentioned object and/or aspects, but do not necessarily have all of them. It should be understood that some aspects of the present technology that have resulted from attempting to attain the above-mentioned object may not satisfy this object and/or may satisfy other objects not specifically recited herein.

Additional and/or alternative features, aspects and advantages of implementations of the present technology will become apparent from the following description, the accompanying drawings and the appended claims.

BRIEF DESCRIPTION OF THE DRAWINGS

For a better understanding of the present technology, as well as other aspects and further features thereof, reference is made to the following description which is to be used in conjunction with the accompanying drawings, where.

Figure 1:
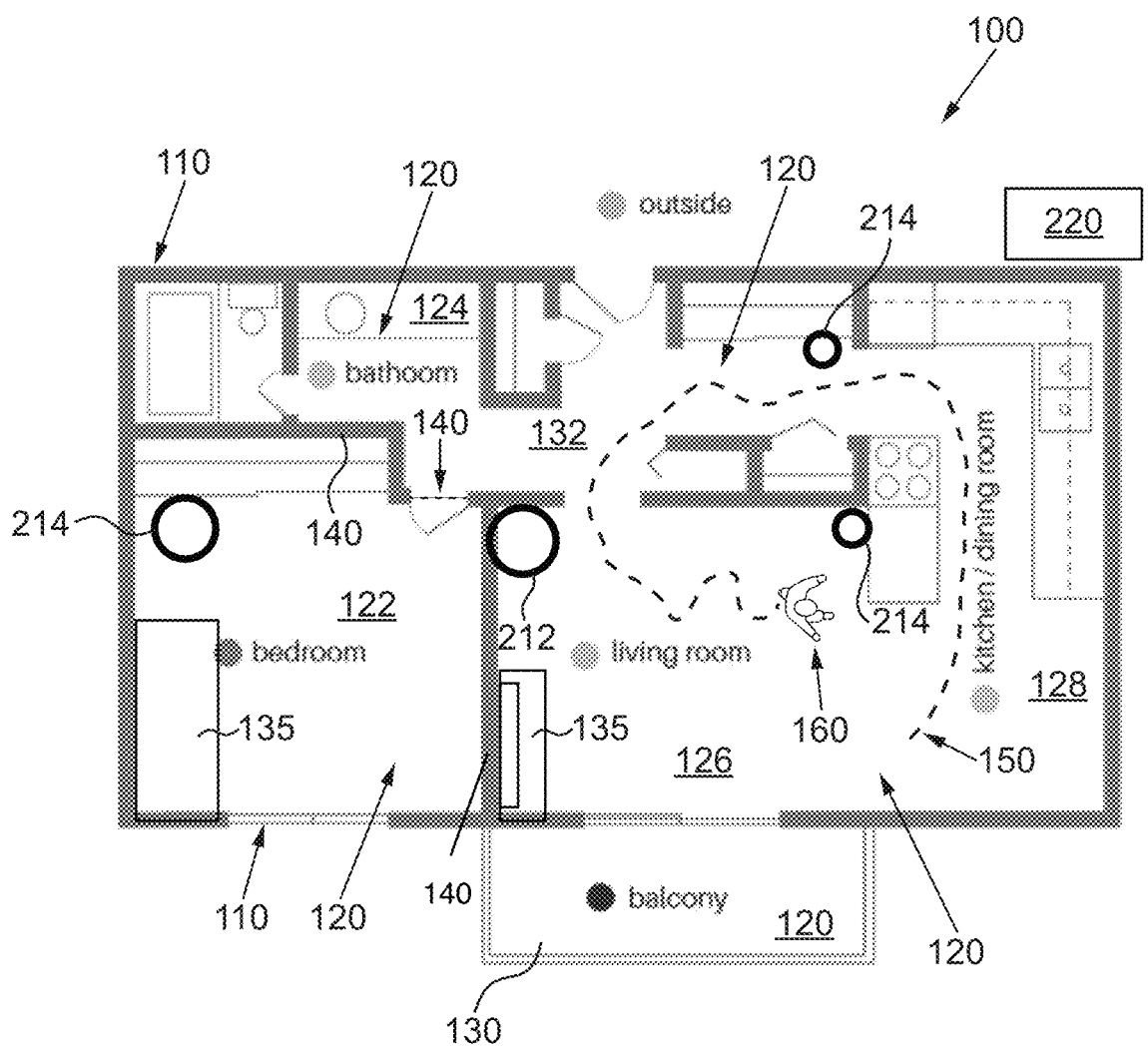
FIG. 1 is a diagram of one embodiment of an environment for implementing embodiments of methods and systems of the present technology.

It should be noted that, unless otherwise explicitly specified herein, the drawings are not to scale.

DETAILED DESCRIPTION

The examples and conditional language recited herein are principally intended to aid the reader in understanding the principles of the present technology and not to limit its scope to such specifically recited examples and conditions. It will be appreciated that those skilled in the art may devise various arrangements which, although not explicitly described or shown herein, nonetheless embody the principles of the present technology and are included within its spirit and scope. Furthermore, as an aid to understanding, the following description may describe relatively simplified implementations of the present technology. As persons skilled in the art would understand, various implementations of the present technology may be of a greater complexity.

In some cases, what are believed to be helpful examples of modifications to the present technology may also be set forth. This is done merely as an aid to understanding, and, again, not to define the scope or set forth the bounds of the present technology. These modifications are not an exhaustive list, and a person skilled in the art may make other modifications while nonetheless remaining within the scope of the present technology. Further, where no examples of modifications have been set forth, it should not be interpreted that no modifications are possible and/or that what is described is the sole manner of implementing that element of the present technology.

Moreover, all statements herein reciting principles, aspects, and implementations of the present technology, as well as specific examples thereof, are intended to encompass both structural and functional equivalents thereof, whether they are currently known or developed in the future. Thus, for example, it will be appreciated by those skilled in the art that any block diagrams herein represent conceptual views of illustrative circuitry embodying the principles of the present technology. Similarly, it will be appreciated that any flowcharts, flow diagrams, state transition diagrams, pseudo-code, and the like represent various processes which may be substantially represented in computer-readable media and so executed by a computer or processor, whether or not such computer or processor is explicitly shown.

The functions of the various elements shown in the figures, including any functional block labeled as a "processor", may be provided through the use of dedicated hardware as well as hardware capable of executing software in association with appropriate software. When provided by a processor, the functions may be provided by a single dedicated processor, by a single shared processor, or by a plurality of individual processors, some of which may be shared. In some embodiments of the present technology, the processor may be a general purpose processor, such as a central processing unit (CPU) or a processor dedicated to a specific purpose, such as a digital signal processor (DSP). Moreover, explicit use of the term a "processor" should not be construed to refer exclusively to hardware capable of executing software, and may implicitly include, without limitation, application specific integrated circuit (ASIC), field programmable gate array (FPGA), read-only memory (ROM) for storing software, random access memory (RAM), and non-volatile storage. Other hardware, conventional and/or custom, may also be included.

Software modules, or simply modules which are implied to be software, may be represented herein as any combination of flowchart elements or other elements indicating performance of process steps and/or textual description. Such modules may be executed by hardware that is expressly or implicitly shown. Moreover, it should be understood that module may include for example, but without being limitative, computer program logic, computer program instructions, software, stack, firmware, hardware circuitry or a combination thereof which provides the required capabilities.

With these fundamentals in place, we will now consider some non-limiting examples to illustrate various implementations of aspects of the present technology.

Certain aspects of the present technology are directed to methods and systems for mapping a given environment in terms of determining (i) a functional identity of a zone in the given environment, and (ii) an identity of one or more of an outer boundary or an inner boundary in the given environment. Other aspects of the present technology are directed to monitoring or tracking a body in the given environment, which may or may not have been mapped by embodiments of the methods and systems for mapping a given environment. Monitoring the body can include determining deviations from a baseline pattern of movement for the purposes of medical diagnosis for example.

Certain embodiments of the methods and systems of the present technology will be described below in relation to home surveillance of a body in the given environment, such as a person residing in a residential home. However, it will be appreciated that the present methods and systems are not limited to home surveillance use.

Broadly, there is provided methods and systems for mapping the given environment comprising determining a pattern of movement of the body in the given environment in a given time period; and determining a functional identity of at least one zone in the given environment based on the pattern of movement of the body to obtain a mapped given environment.

From another broad sense, there is also provided methods and systems for mapping the given environment comprising determining a trajectory of the body in the given environment over the given time period and determining, based on the trajectory of the body in the given environment, one or more of an outer boundary of the given environment, and an inner boundary of the given environment.

Environment and Zones

FIG. 1 shows an example environment 100, in which non-limiting embodiments of different aspects of the present technology may be implemented. The environment 100 of FIG. 1 is a residential home. Without limitation, the residential home may be a single apartment with adjoining apartments (not shown) on the same floor or other apartments below or above.

The environment 100 is defined by an outer boundary 110. The environment 100 has a number of zones 120 within the outer boundary 110. Zones 120 may be rooms or areas. In FIG. 1, the zones 120 of the environment 100 comprise a bedroom 122, a bathroom 124, a living room 126, a kitchen/dining zone 128, a balcony 130, and a hallway 132. Some of the zones 120 are defined by inner boundaries 140, such as walls and/or doors. Other zones 120 are not defined or separated by walls (e.g. the living room, and kitchen/dining room which have an open plan configuration), and are open plan. The environment 100 also has one or more inanimate objects 135 such as furnishings, for example a sofa, a bed, a refrigerator, cabinets, a bath tub, a sink, a toilet, and a cooker.

A body 160 may move, at least occasionally, within the given environment 100 from one zone 120 to another zone 120, and within zones 120. The location of the body 160 in the given environment 100, a trajectory of the body 160 in the given environment 100, and patterns of movement of the body 160 in the given environment 100, as well as other parameters, may be tracked and monitored by embodiments of the systems and methods as described herein.

The tracked movement of the body 160 may include the path of the body 160 and/or the motions of the body 160, both of which are referred to herein as "movement." The path of the body 160 from position to position within the given environment 100 may be tracked and monitored. For example the movement of the body 160 from a first zone 120 to a second zone 120, or within a zone 120, may be tracked and monitored. The motions of the body 160 while at a fixed position or while moving may be tracked and monitored.

The motions of the body 160 detected may include a type of movement of the body 160 in the given environment 100 (e.g. motion associated with falls, range of motion, etc.) For example if the body 160 is moving their hand, the motion of the hand may be detected. Radar signals (baseband and/or Doppler) may be used to detect the motions of the body 160. Events and activities, such as falls, activities of daily living, etc., may be identified based on the radar signals.

Radar signatures corresponding to the body 160 may be identified, and an MLA may use the radar signatures to determine an activity that the body 160 is performing. The location of the body 160 may also be used by the MLA to identify the activity. For example the MLA may be provided the functionality of a room that the body 160 is in, such as an indication that the body 160 is in a kitchen, bathroom, etc. The functionality of the room may improve the accuracy of predicting the activity being performed. For example inputting the functionality of the room may aid the MLA in discriminating between similar radar signatures.

To train the MLA, the radar signatures may be labelled by identifying an activity corresponding to the radar signatures. For example, if a user inputs that they are vacuuming during a specified time period, radar signatures collected during that time period may be labelled as radar signatures for vacuuming. The MLA may then be trained, using the labeled radar signature data, to predict an activity being performed by the body 160.

At least some of the zones 120 have a functional identity. The functional identities of the zones 120 may be the same or different, or may be combinations of different functions. Non-limiting examples of zones 120 and their functional identities comprise a living zone (e.g. a living room), a sleeping zone (e.g. a bedroom), an eating zone (e.g. a dining room), a food preparation zone (e.g. a kitchen), a bathroom zone (e.g. a bathroom), a passage zone (e.g. a corridor), an entrance zone (e.g. a hallway), a sitting zone (e.g. a tv room), a recreational zone (e.g. a playroom), an outdoor zone (e.g. a balcony or a garden).

It is contemplated that, in certain embodiments, knowledge of the identity of the zone can help in monitoring the body 160 in the given environment 100. In certain embodiments, knowledge of the inner and outer boundaries 140, 110 can help in monitoring the body 160 in the given environment 100. For example, in embodiments where the environment 100 is the home of an elderly or infirmed person, such monitoring can provide certain biomarkers about the body 160 by tracking times spent in particular zones, types of activities performed in particular zones, and/or types of movements performed in particular zones (such as slow walking), which may be indicators of certain conditions. For example, longer times spent by the body 160 in bed per day can indicate depression; more frequent visits to the bathroom per day by the body 160 may indicate a bladder infection; and pacing may indicate Alzheimer's.

It will be clear to skilled persons that the environment 100 of the present technology may differ from that illustrated in FIG. 1, in that the environment 100 may have a different configuration, a different layout and/or different zones. Some or all of the zones 120 may be separated by walls, or have an open-plan configuration (no wall separation).

The environment 100 may also have a different purpose than that of the environment 100 depicted at FIG. 1. Instead of being a residence, the environment 100 may be at least a portion of a hospital, a clinic, a laboratory, a rehabilitation centre, a sports medicine setting, a gym, a school, a clinical trial setting, a prison, a detention centre, a laboratory, a zoo, or any other setting. In other embodiments, the environment 100 is a home and the purpose of mapping the environment is for assisting first responders and/or for intrusion detection. Accordingly, the body 160 may be that of an occupant, a patient, an elderly resident, a child, a prisoner, an intruder, an animal etc.

System—Overview

Figure 2:
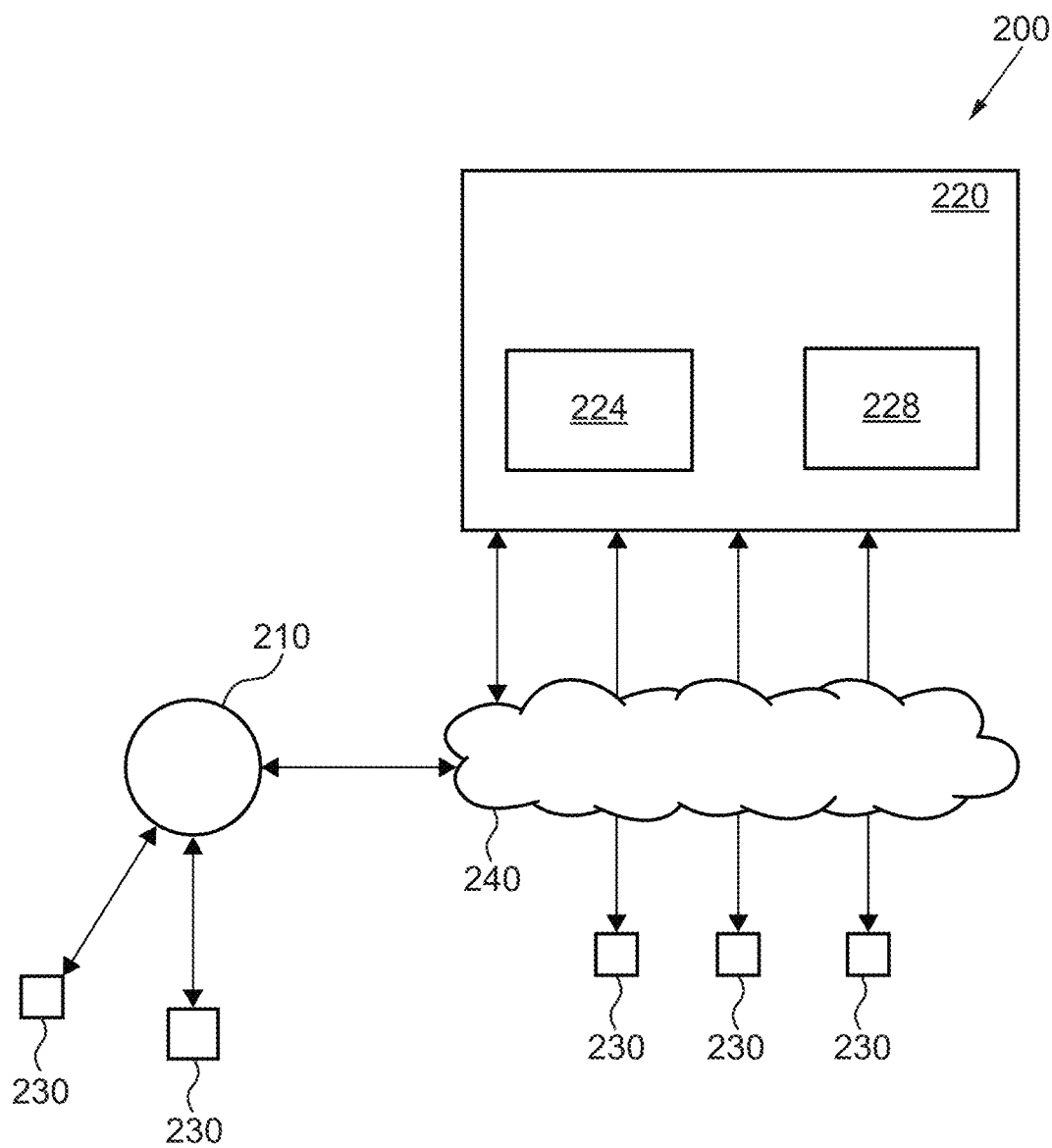
FIG. 2 is a diagram of a system for mapping a given environment, in accordance with an embodiment of the present technology.

Turning now to FIG. 2, which shows a system 200 for mapping functionalities of a given environment, for mapping boundaries of a given environment and/or for monitoring/tracking movement of a body 160 within a given environment, such as the body 160 in the environment 100 of FIG. 1 in accordance with at least one non-limiting embodiment.

The system 200 comprises a mapping device 210 for transmitting and detecting radio frequency (RF) signals, which is operatively communicable with a computer system 220 for executing methods of the present technology. The system 200 may also comprise one or more sensors 230, operatively communicable with the computer system 220, for detecting various signals, such as relating to the environment 100 or the body 160. The system 200 may be provided with more than one mapping device 210, more than one computer system 220, and/or more than one sensor 230. In certain embodiments, the system 200 comprises one mapping device 210, one computer system 220 and a plurality of sensors 230.

In certain embodiments, the computer system 220 and/or the sensor 230 may be implemented within the mapping device 210. In certain embodiments, at least some of the sensors 230 are incorporated in the mapping device 210.

Figure 4:
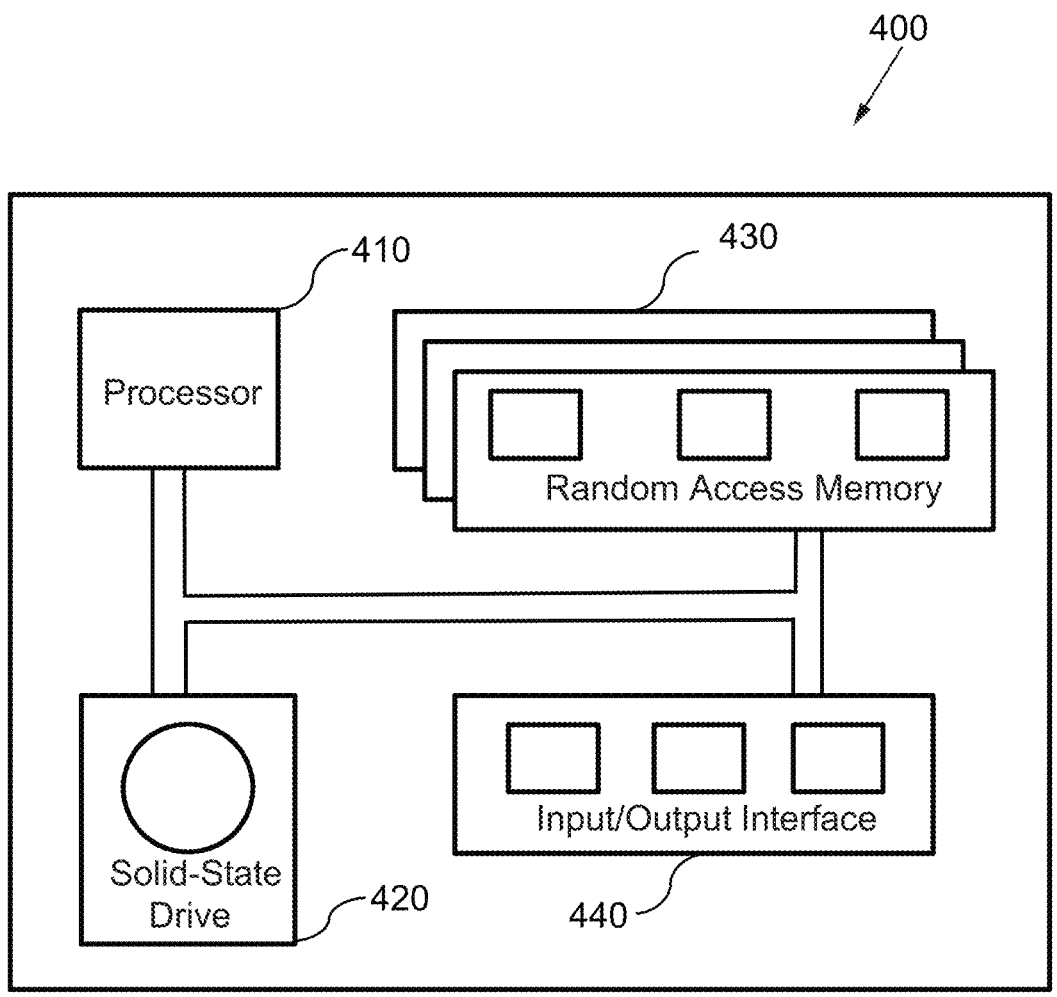
FIG. 4 is a diagram of one embodiment of a computing environment implementing embodiments of the methods and systems of the present technology.

In the embodiment of FIG. 1, the mapping device 210 and the sensor 230 are positioned within the outer boundary 110 in the environment 100. The computer system 220 is positioned remotely of the environment, such as in a server, or other device, and will be described later with reference to FIG. 4. In other embodiments, the computer system 220 is distributed across a device (not shown) arranged to be positioned in the environment and another device (not shown) positioned remotely of the environment, such as in the cloud.

In some embodiments, the mapping device 210, the sensor 230, and the computer system 220 are configured to communicate directly or indirectly with each other (for example via a communication network 240). The communication network 240 may be the Internet and/or an Intranet. Multiple embodiments of the communication network 240 may be envisioned and will become apparent to the person skilled in the art of the present technology.

In some embodiments, the mapping device 210 and/or the sensor 230 may be connected to each other and/or communicate with each other via the computer system 220. In some embodiments, any two or more of the mapping device 210, the sensor 230 and/or the computer system 220 are provided as an integral device.

In some embodiments, the mapping device 210, the sensor 230, and the computer system 220 communicate at predetermined times, for example for sending data to each other in batches.

Mapping Device

Figure 3:
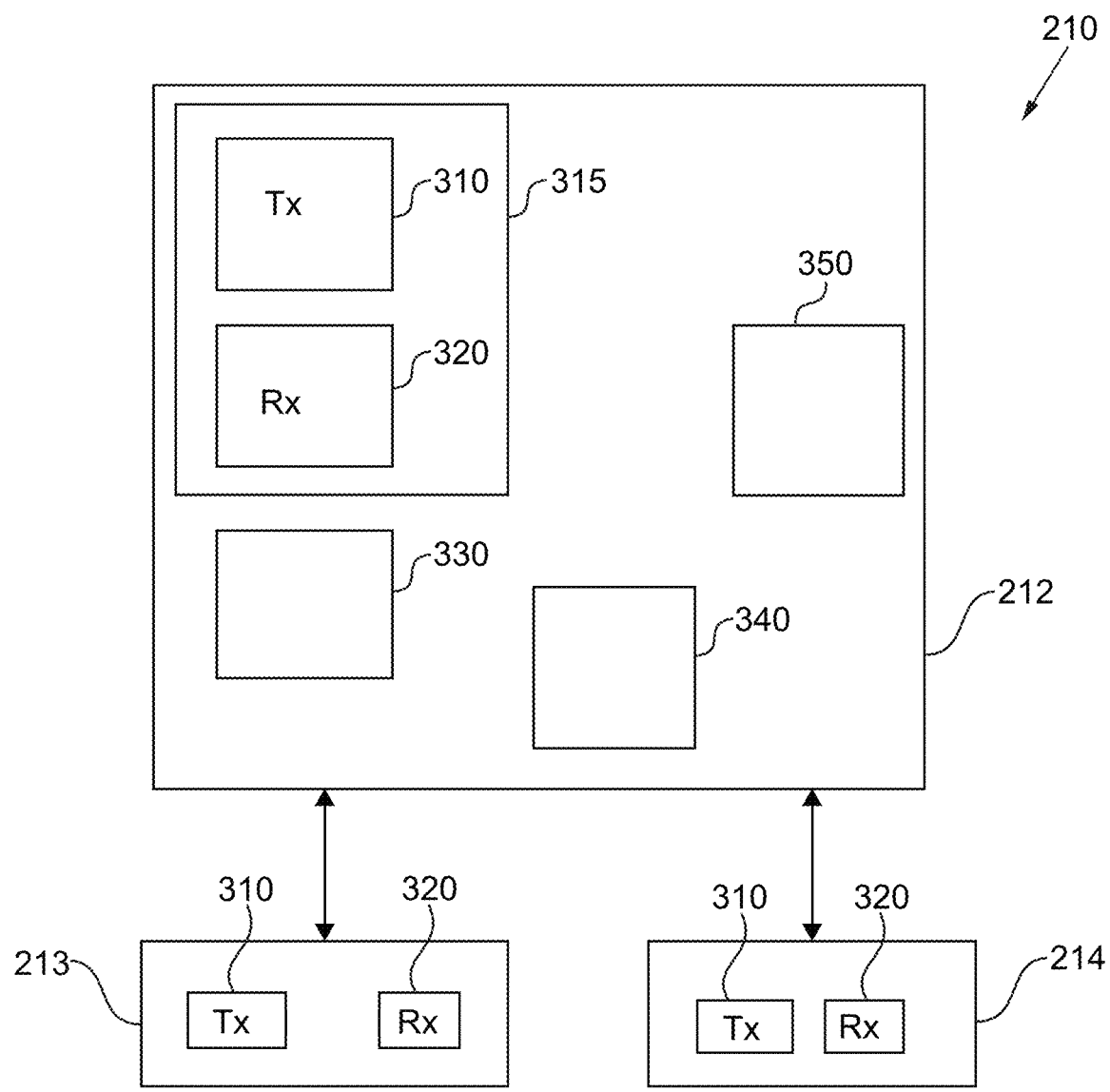
FIG. 3 is a diagram of a mapping device, in accordance with an embodiment of the present technology.

Referring now to FIG. 3 showing certain embodiments of the mapping device 210. In certain embodiments, the mapping device 210 comprises a plurality of units which may have a hierarchical configuration or flat configuration (same hierarchical level). In certain embodiments, the mapping device 210 comprises a single unit. In the example of FIG. 3, the mapping device 210 has a first unit 212, a second unit 213, and a third unit 214 which are arranged in a hierarchical configuration. In this embodiment, the first unit 212 is a main unit 212 operatively communicable with the first and second units 213, 214 which are satellite units. One or more of the first, second and third units 212, 213, 214 of the mapping device 210 comprise one or more of a transmitter 310 configured to emit (transmit) radio frequency signals, a receiver 320 configured to receive (detect) radio frequency signals (which may be implemented as a transceiver 315, also known as an antenna), a processor 330 configured to process the radio frequency signals, a random-access memory (RAM) 340, and a communication module 350 configured to enable communication of information between one or more of the satellite units 213, 214, the main unit 212, and the computer system 220. As noted above, the mapping device 210 may further comprise the computer system 220. Units 212, 213, 214 may include other sensors such as a microphone (not shown), a magnetometer, accelerometer, thermometer, barometric pressure sensor, gyroscope, luminosity meter, proximity sensor, camera, film camera etc. The additional information from these sensors can provide further information regarding a position of the body 160 in the environment 100, or can help to identify the body through its signature.

In certain embodiments, the mapping device comprises a base and a cover defining a hollow body. One or more of the transmitter, the receiver, and the sensors, are positioned in the hollow body. A plug extends from the base, for communication with a socket, for supplying power to the mapping device. The cover is removeably attachable to the base, such as by a fastener (e.g. screw, clip, nail etc.), or by a snap-fit. In certain embodiments, the cover includes at least one opening or at least one window, with a sensor positioned adjacent the opening or window. For certain sensor types, this can facilitate signal detection such as in the case of a microphone or a luminosity meter.

The mapping device 210 may also be arranged to connect, with or without a wire, to connectable devices such as a medication box, a wallet, a key chain, a bag, and the like. In this way, certain embodiments of the present technology may also be used to help locate the connectable device within the given environment.

One such mapping device 210 comprises a radar device which can transmit and receive radio frequency waves and therefore measure distance and movement. The mapping device 210 may also include functionality to measure respiratory rate and heart rate.

Referring back to FIG. 1, in certain embodiments, the main unit 212 and the satellite units 213, 214 can be positioned in any manner in the environment 100. The satellite units 213, 214 can be positioned in the same or different zone 126 as the main unit 212. The satellite units 213, 214 can be positioned in the same or different zone 122 to each other.

In at least one embodiment, the mapping device 210 is arranged to be stationary or immobile in the environment 100 during use, such as resting on, or mounted to, a structure of the environment 100 (e.g. a wall, a floor, a ceiling, a power socket). By mounted is meant removably or permanently attached. The mapping device 210 may also be arranged to rest on a flat surface such as a table, an appliance, an immobile furnishing in the environment 100. In certain embodiments, the mapping device 210 does not require being carried or being worn on the body 160, in other words, the mapping device 210 is not a wearable device. In certain embodiments, the mapping device 210 comprises a combination of wearable and non-wearable units. In certain embodiments, the mapping device 210 is connectable to an electrical outlet.

In certain embodiments, any of the first, second and third units 212, 213, 214 are arranged to be mounted to an electrical outlet in the given environment. In certain embodiments, any of the first, second and third units 212, 213, 214 are arranged to be mounted to wall(s) of the given environment at a height of the electrical outlet, such as about 30 cm to about 40 cm from a floor of the given environment. In certain other embodiments, any of the first, second and third units 212, 213, 214 are arranged to be mounted to wall(s) of the given environment at a height of between about 50 cm to about 500 cm, about 50 cm to about 150 cm, about 50 cm to about 140 cm, about 80 cm to about 120 cm, about 95 cm to about 105 cm, about 90 cm to about 110 cm, about 100 cm to about 135 cm from the floor of the environment 100. The height, and/or an angle of radio frequency transmission/detection, may be selected in order to detect the body 160 in the environment 100 whilst avoiding or minimizing detection of other systems in other environments close to or adjoining the environment 100.

In some embodiments, the connection between one or more of the first, second and third units 212, 213, 214 may be wired. In some other embodiments, the connection between one or more of the first, second and third units 212, 213, 214 is wireless. In some embodiments, data is sent from the mapping device 210 to the computer system 220 for storage in a database, and/or for use as an input to training a machine learning algorithm.

In certain embodiments, units of the mapping device 210 are positioned on or along the outer boundary 110 of the given environment 100, for example, along external walls as opposed to internal partition walls. For embodiments of the mapping device 210 with three or more units, the units should be arranged relative to one another in a triangular configuration i.e., not be aligned.

In certain embodiments of the present technology, the mapping device 210 does not require a set-up phase and is able to map the given environment, in a plug-and-play type functionality. In this respect, the plurality of units 212, 213, 214 of the mapping device 210 are able to communicate with one another and the computer system 220. The computer system 220 is arranged to determine the relative location of each of the units 212, 213, 214 based on the data from each of the units 212, 213, 214. By relative location is meant one or both of distance and orientation. For example, if all three units 212, 213, 214 are installed on the outer boundary 110 of the given environment 100, information on the orientation of the units 212, 213, 214 will help to determine whether or not they have been installed on the same or on different walls. If the units 212, 213, 214 are all installed on different walls, then the location of these outer walls (outer boundary 110) and the dimension of at least one of the walls can be derived.

In certain embodiments, the mapping device 210 is configured to transmit and receive radio frequency signals. The technology used may include, but is not limited to, any type of continuous wave or pulsed radars.

For example, the mapping device 210 may be configured to transmit and receive radio frequency signals between about 2.4 GHz to about 80.0 GHz, or about 3.0 to about 10.7 GHz.

In at least one embodiment, the mapping device 210 is configured to emit and receive an ultra-wide band (UWB) signal. UWB signal transmits at low energy levels and is adapted to be used for short-range transmission over a large portion of the radio spectrum. A person skilled in the art may appreciate that UWB signal may not interfere with conventional narrowband transmission in the same frequency band. UWB signals transmitted between the first, second, and/or third units 212, 213, 214 may be used to determine a distance between each of the units 212, 213, 214. The time of flight of the UWB signals between the units 212, 213, 214 may be calculated and used to determine the distances between the units 212, 213, 214.

Some or all of the units 212, 213, and 214 may include sensors, such as the sensors 230 described below. For example, the units 212, 213, and 214 may include microphones, pressure sensors, air quality sensors, and/or other sensors.

Sensors

Referring now to the sensors 230 shown in FIG. 2, communicatively coupled to the computer system 220 and/or the mapping device 210. The sensors 230 may be integral with the mapping device 210 and/or the computer system 220. The sensors 230 are able to obtain various data signals about the environment 100 or the body 160 which can help the system 200 to map the environment 100, functionally or in terms of its boundaries 110, 140, as well as to monitor the body 160.

In certain embodiments, the sensors 230 are configured to detect and measure signals including, but not limited to, various environmental (contextual) parameters. Contextual parameters include, but are not limited to, sound, video, vibration, humidity, temperature, light, light intensity, luminosity levels, UV levels, electromagnetic radiation, air composition, carbon dioxide levels, oxygen levels, and air pressure. Contextual data can also include time of day, day of week, season, geolocation and weather conditions. An example of a use of vibration data could be to use vibration induced by a washing machine, a blender, a television speaker, or the like to identify a room. In another example, one or more of the mapping device units are made to vibrate, and the vibration signal detected by the sensor 230. One of the sensor 230 and the mapping device could have a known location in order to derive the location of the other.

Non-limiting examples of sensors may comprise an accelerometer, a thermometer, an ultra-violet (UV) sensor, an atmospheric humidity sensor, an atmospheric pressure sensor, a $CO_2$ sensor, an $O_2$ sensor, a gas composition sensor, a light level sensor, a colour sensor, a gyroscope, and a microphone. Accordingly, the signals detected by the sensor 230 may comprise contextual data temperature data, atmospheric data, visual data, audio data, composition data, etc.

The sensors 230 may also be adapted to capture images and transmit them to the mapping device 210 and/or computer system 220. The sensor 230 can be an image capturing device, such as a video camera. In some embodiments, the video camera is configured to capture images and/or videos of the user's face. This image data may be converted to another form of data through face recognition software, for example. The sensor 230 may also be an infrared camera of RF camera. The sensor 230 may also be a geo-positioning system (GPS).

In certain embodiments, the sensors 230 are configured to detect and measure signals including, but not limited to, various physiological parameters about the body 160. Physiological parameters include, but are not limited to respiratory rate, heart rate, voice, movement of limbs (e.g. flailing), movement of eyelids, position of torso, temperature, breath composition, carbon dioxide levels, oxygen levels, and stress.

Non-limiting examples of such sensors 230 arranged to detect the physiological parameters comprise a thermometer, a microphone, and a video. Accordingly, the signals detected by the sensor 230 may comprise physiological data such as respiratory rate data, heart rate data and/or other heart data, voice data, movement of limbs (e.g. flailing) data, movement of eyelids data, position of torso data, temperature data, breath composition data, carbon dioxide level data, oxygen level data, and stress.

In certain embodiments, the physiological data is obtained from the mapping device 210. For example, the mapping device 210 may be arranged to derive respiratory rate data, heart rate data, eye movement data, limb movement data and other movement data from the detected radio frequency signals of the body 160. In certain embodiments, the sensor 230 is a wearable device for detecting and measuring physiological data. The wearable sensor 230 may comprise an accelerometer, a gyroscope, a temperature sensor, a photoplethysmography sensor, an electrode sensor (ECG, EEG, EMG), a pressure sensor, a force sensor, a stretch sensor, a glucose sensor, a blood oxygen sensor, a hydration sensor, a GPS sensor, etc.

In certain embodiments, one or more sensors 230 may also provide directional information. For example, a plurality of aligned microphones may be provided and based on a loudness of the detected sound, a direction of the source of the sound can be identified.

In some embodiments, the sensors 230 may be arranged to receive instructions from the computer system 220, such as, but not limited to, command values for turning on the sensor, turning off the sensor, and/or sending data. In some embodiments, one or more of the mapping device 210 and the sensors 230 may be commanded independently, in accordance with dedicated control values. For example, but without being limiting, control values may comprise a Boolean value (signal_ON, signal_OFF) or other type of values which may become apparent to the person skilled in the art of the present technology.

In certain embodiments, the sensors 230 comprise a communication module (not shown) for receiving and transmitting data to and/or from the computer system 220 or the mapping device 210. In some embodiments, the connection between one or more of the sensors 230 and the computer system 220 may be wired. In some other embodiments, the connection between the sensors 230 and the computer system 220 is wireless. In some embodiments, data is sent from the sensors 230 to the computer system 220 for storage in a database, and for use as an input to training a machine learning algorithm.

Computer System and Computing Environment

Turning now to the computer system 220. In certain embodiments, the computer system 220 is implemented in a computing environment 400. In certain embodiments, the computing environment 400 is at least partially embodied in the mapping device 210. The computer system 220 depicted in FIG. 2 comprises a processor 224 and a database 228.

In some embodiments, the computing environment 400 comprises various hardware components including one or more single or multi-core processors collectively represented by a processor 410, a solid-state drive 420, a random access memory (RAM) 430 and an input/output interface 440. Communication between the various components of the computing environment 400 may be enabled by one or more internal and/or external buses (e.g. a PCI bus, universal serial bus, IEEE 1394 "Firewire" bus, SCSI bus, Serial-ATA bus, ARINC bus, etc.), to which the various hardware components are electronically coupled. The processor 410 may be the processor 224, and the database 430 may be the database 228.

The input/output interface 440 may allow enabling networking capabilities such as wire or wireless access. As an example, the input/output interface 440 may comprise a networking interface such as, but not limited to, a network port, a network socket, a network interface controller and the like. Multiple examples of how the networking interface may be implemented will become apparent to the person skilled in the art of the present technology. For example, but without being limiting, the networking interface may implement specific physical layer and data link layer standard such as Ethernet, Fibre Channel, Wi-Fi or Token Ring. The specific physical layer and the data link layer may provide a base for a full network protocol stack, allowing communication among small groups of computers on the same local zone network (LAN) and large-scale network communications through routable protocols, such as Internet Protocol (IP).

According to implementations of the present technology, the solid-state drive 420 stores program instructions suitable for being loaded into the random access memory 430 and executed by the processor 410 for executing methods for mapping the environment 100 (in terms of functionalities or boundaries) and/or monitoring a body 160 in the environment 100. For example, the program instructions may be part of a library or an application.

In certain embodiments, the computing environment 400 is implemented in a generic computer environment, such as a generic computer system e.g. a conventional computer (e.g. an "off the shelf" generic computer system). The generic computer system may be an electronic device such as, but not limited to, a desktop computer/personal computer, a laptop, a mobile device, a smart phone, a tablet device, a server, or a wearable device such as a smart watch.

In certain embodiments, the computing environment 400 is implemented in a device specifically dedicated to the implementation of the present technology. For example, the computing environment 400 may be implemented in an electronic device such as, but not limited to, a desktop computer/personal computer, a laptop, a mobile device, a smart phone, a tablet device, a server, specifically designed for mapping the environment and/or monitoring/tracking a body 160 in the environment, or be dedicated to operating other devices for mapping the environment and/or monitoring the body 160 in the environment.

In some embodiments, the computer system 220 is hosted on a server installed within or in a vicinity of the environment 100. In some alternative embodiments, the computer system 220 may be partially or totally virtualized through a cloud architecture. In some embodiments, data is received by the computer system 220 from the mapping device 210 for storage in the RAM or another database, and for use as an input to training a machine learning algorithm.

In some embodiments, the computing environment 400 has a user interface. The user interface may be used for any one or more of (i) set-up of the system 200, where required, (ii) validation of the mapping, where required, (iii) for communication with the body 160, and (iv) for receiving direct communications from the body 160. The user interface may be a screen, a microphone, a speaker, buttons etc.

In certain embodiments, the computer system 220 is implemented as a smart home device of the type Amazon™ Echo™, Google™ Home™, Google™ Nest™, Apple™

HomePod™ device or the like. In these cases, the present technology may add additional functionality to these home devices by incorporating the mapping device 210 and sensor 230 functionality.

In some embodiments, the computing environment 400 may be distributed amongst multiple systems. In some embodiments, the computing environment 400 may be at least partially implemented in another system, as a subsystem for example. Any one or more of the sensors 230, the mapping devices 210, and the computer system 220 may be incorporated into a single device or be distributed across separate devices in any combination thereof appropriate to the relevant task at hand. The computing environment as described herein may be implemented in that single device.

As persons skilled in the art of the present technology may appreciate, multiple variations as to how the computing environment 400 is implemented may be envisioned without departing from the scope of the present technology.

In certain embodiments, the computer system 200 or the processor 410 is arranged to execute, a machine learned algorithm (MLA) for determining, by the MLA, the functional identity of the zone 120 in the environment or for mapping the boundaries of the environment 100.

The machine-learning algorithm, implemented by the computer system 200, may comprise, without being limitative, a non-linear regression, a linear regression, a logistic regression, a decision tree, a support vector machine, a naïve Bayes, K-nearest neighbors, K-means, random forest, dimensionality reduction, neural network, gradient boosting and/or adaboost MLA.

In some embodiments, the MLA may be re-trained or further trained by the system 200 based on a verification of the functional identity of the at least one zone as determined. In certain embodiments, the system 110 is also arranged to execute a training phase of the MLA. In other words, an output from the system 100 is fed back into the MLA for training or re-training. Training inputs may include data from the sensors 230, and other sources. The training data may include data about the body 160, or data about the given environment 100.

Operation—Methods
Tracking Location—Triangulation

The system 200 is configured to determine and track a location of the body 160 at specific points in time and in given time periods. To obtain the location of the body 160, the transceiver 315 (or transmitter 310) of the mapping device 210 emits the signal which, at least partially, reflects from the outer boundary 110, inner boundaries 140, inanimate objects 135 and the body 160. The transceiver 315 (or detector/receiver 320) may, at the same time, receive/capture the radio frequency (RF) signal, which include the reflection from the inanimate objects 135 and the body 160. A portion of the signal emitted by the transceiver 315 (or transmitter 310) may also propagate through the outer boundary 110, inner boundaries 140, inanimate objects 135 and the body 160.

The emitted and captured signals at the transceivers 315 may provide information on the location of the body 160 at a particular time stamp. The emitted and captured signals at the transceivers 315 may provide information indicating the speed and/or direction of movement of the body 160. Objects (e.g. the body 160 and/or inanimate objects 135) may be located using triangulation and/or trilateration in manners known in the art. In certain embodiments, the system 200 uses triangulation to locate the body 160 at a particular time stamp.

In at least one embodiment, the data regarding the emitted and captured signals by the transceivers 315 is transmitted to the computer system 220 or the processor 330 of the mapping device 210 for processing of the data to determine the location of the body 160.

In at least one embodiment, the system 200 is configured to process the detected RF signals and to identify any one or more of the body 160, the outer boundary 110, the inner boundary 140, and inanimate objects 135.

In certain embodiments, it is possible to triangulate the position of the body 160 in the environment 100 using moving reflections. The body 160 when static can be located by identifying small movements generated by breathing or by periodic movements with well defined frequency range such as from the beating heart. The body 160 can also be identified using a signature associated with the body, such as a physiological parameter (e.g. breathing rate, other vital signs etc.), or a physical parameter (e.g. a shape, a silhouette, a height, a gait pattern, a movement pattern, etc.).

The units 212, 213, and 214 may be able to track the body 160 without having line-of-sight to the body 160. As described above, the RF signals may pass through boundaries such as walls. Because the RF signals pass through walls, the body 160 might be detected and/or tracked even when the body 160 is in a room that does not contain one of the units 212, 213, and 214.

Tracking Location—Non-Triangulation

In other embodiments, triangulation is not required for identification of the location of the body 160. In these embodiments, a location of the body 160 can be determined using a combination of a detected RF signal with another type of signal or data associated with the activity, the function or the zone. The other type of signal or data can be a physiological data signal or physiological data, a contextual data signal or contextual data, such as determined by the sensors 230 or from any other source.

In one embodiment, the RF signal data from at least one of the units 212, 213, 214 is combined with sound data from a microphone sensor 230 in one of the units 212, 213, 214 of the mapping device 210. The sound data can be mapped onto the RF data as a function of time, for example, to further pinpoint the location of the body 160 as determined by the mapping device 210. In such embodiments, triangulation of the RF signals is not required.

For example, sound data identified as snoring could be combined with RF data from any one or more of the units 212, 213, 214 to narrow the functionality of the room to the bedroom or other zone where the body 160 sleeps. In another example, sound data identified as running water could be attributed to the bathroom or kitchen (shower, washing up or toilet flush) to narrow the functionality of the zone to the bathroom or kitchen. In yet another example, radar signals (baseband or Doppler), i.e. movement data, may be used to determine a specific activity signature, such as sleeping, which may be used to determine the functionality of the room. In this respect, in certain embodiments, data types are initially associated with function(s) (e.g. cooking, sleeping, reading, falling) and/or zone(s) (e.g. kitchen, bedroom, living room). In another example, the sensor 230 may comprise the microphone array, mentioned above, with directionality of detection due to the arrangement of the microphones.

Identification of the location of the body 160 can also be performed using several RF antennas appropriately spaced to detect the direction of an incoming RF signal, and accelerometers to detect the direction of an incoming vibration.

Signatures

In at least one embodiment, a reflection RF signal signature associated with any one or more of the body 160, inanimate objects 135, the outer boundary 110, and the inner boundary 140, may be determined by the mapping device 210. The reflected signal signature may include various parameters such as an intensity (frequency, timing, and/or distance etc.) of the RF signal. The RF signal can also provide an indication of body mass, shape, and/or motions of the body 160, which could be used to characterize the body 160. Time lags between detected RF signals can be taken into consideration for a multipath determination of the any one or more of the body 160, inanimate objects 135, the outer boundary 110, and the inner boundary 140. The signature associated with the body can also include a silhouette, a height, physiological data (e.g. breathing rate), micro-movement data (e.g. gait, range of motion, etc.), as measured by the mapping device 210 or any of the sensors 230.

Location—Trajectory

In at least one embodiment, the system 200 may obtain a location of the body 160 at a specific time using the mapping device 210, as a snap-shot for example. Over a given time period, a plurality of locations of the body 160 can be obtained. The location of the body 160 can be defined in terms of location vectors or co-ordinates. Location vectors may also comprise a direction of movement of the body 160 at each time stamp. For example, this may be calculated by the computer system 220 based on the location of the body 160 in the previous time stamp and the location of the body 160 at the next time stamp.

The plurality of locations of the body 160 can provide a trajectory 150 (see FIG. 6) of the body 160 over a given time period. The trajectory 150 is representative of a path of movement of the body 160 across a two-dimensional plane of the given environment 100, and/or multiple two-dimensional planes, such as in an environment 100 with two or more floors. The trajectory 150 of the body 160 may be stored in a database, which may be the database 228, 430.

The plurality of locations of the body 160 can also provide a pattern of movement of the body 160 in the given time frame. This will be explained further below. The given time frame can be a 24 hour period (a day), a month, a year etc.

Method for Mapping Functionalities of a Given Environment

Figure 5:
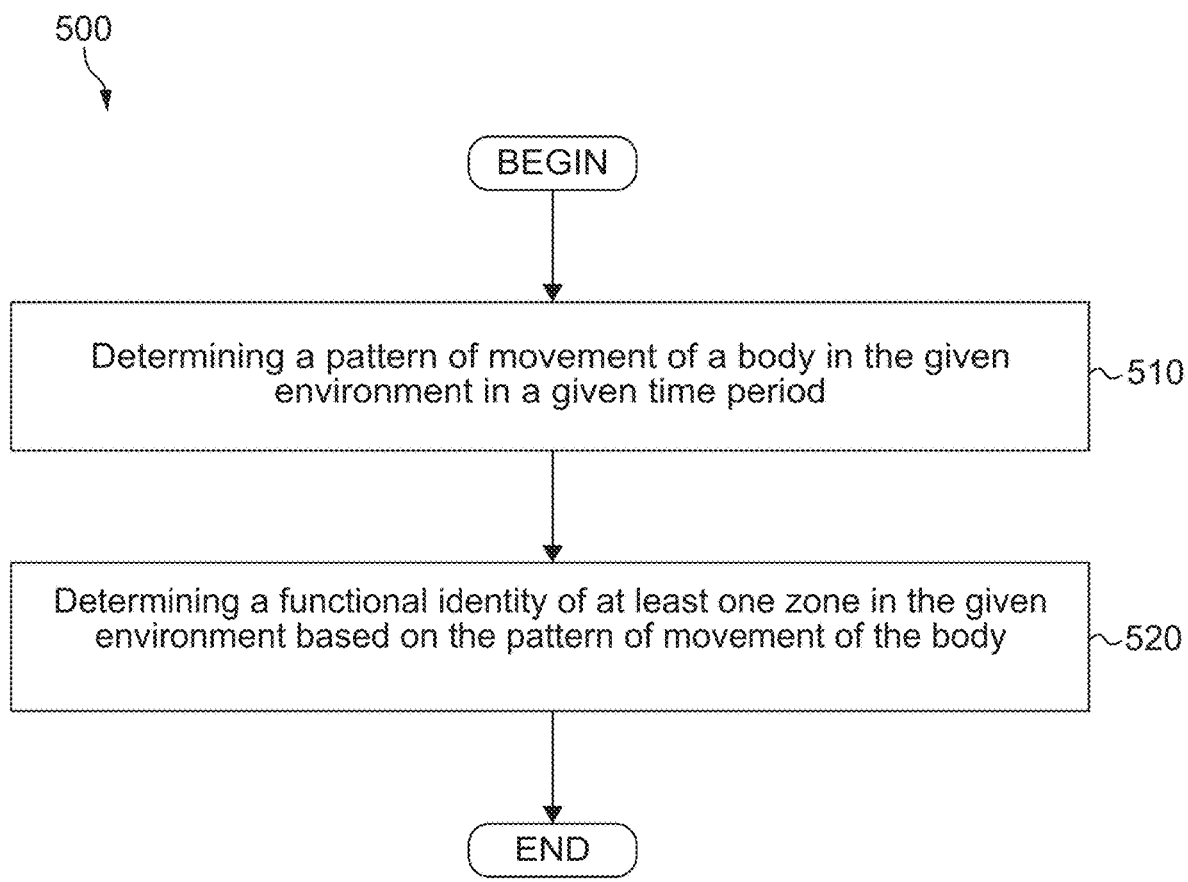
FIG. 5 is a diagram of a method for mapping functionalities in an environment, in accordance with an embodiment of the present technology.

Referring now to FIG. 5, depicted therein is a method 500 for mapping a given environment, such as the environment 100, in accordance with at least one non-limiting embodiment. The method 500 is executable by a processor of a computer system, such as the processor 410 of the computer system 220 as described herein.

At step 510, a pattern of movement of the body 160 is determined in the given environment in a given time period. The given time period may be a predetermined time period, such as a day. The pattern of movement can also be referred to as a localization profile. Optionally, the method 500 comprises a step of tracking the location of the body 160 in the given environment over the given time period. The location of the body 160 can be tracked using the RF signals described herein, or by any other method not limited to RF detection and tracking. In certain embodiments the method 500 includes a step of tracking a location of the body 160 using detected RF signals. A step of transmitting and receiving RF signals, such as using the mapping device 210 may also be included in the method 500.

The pattern of movement may be derived from a trajectory or trace, in two-dimensions, or multiple two-dimensional planes, of the movement of the body 160 across the given environment 100 and including information regarding the time stamp or recurrence of being located at one or more coordinates or vectors. In certain embodiments, the pattern of movement is defined by a sequence of co-ordinates or location vectors of the location of the body 160 as a function of time.

Pattern of movement can mean an average of a plurality of patterns of movement (trajectories) obtained for the body 160 in different given times. For example, the location of the body 160 can be tracked every day for a week, and the pattern of movement which is determined is the average of the daily trajectory.

The pattern of movement is indicative of a daily living habit of the body 160 and can be used to determine the functional identity of zones 120 in the environment 100. In certain embodiments, the pattern of movement may be one or more of: (i) number of visits to a certain locations in the given environment 100 in a given period, (ii) relative time spent in certain locations in the given environment 100 by the body 160 in a given period, (iii) time(s) of day spent in certain locations of the given environment 100 by the body 160 in a given period, (iv) a sequence of locations of the body 160 in certain locations of the given environment 100 in the given time period, (v) frequency of location in the certain locations in the given environment 100, and/or (vi) motions that are specific to an activity or event (sitting, eating, sleeping, etc.).

The pattern of movement may be collected and then stored in a database, such as the database 228.

At step 520, the identity of at least one zone 120 in the given environment 100 is determined based on the pattern of movement of the body 160 and/or motions of the body 160.

Determining the identity of the at least one zone 120 in the given environment 100 can comprise grouping together certain of the co-ordinates or location vectors based on a commonality or similarity of the co-ordinates or location vectors in terms of at least one of:

(i) a physical proximity of the co-ordinates or location vectors to one another, (ii) a duration of time spent at certain of the co-ordinates or location vectors by the body 160 in a predetermined time interval, (iii) a time(s) of day of location of the body 160 at certain co-ordinates or location vectors in the predetermined time interval, (iv) a sequence of location of the body 160 at certain co-ordinates or location vectors in the predetermined time interval, (v) a frequency of location of the body 160 at certain co-ordinates or location vectors in the predetermined time interval, (vi) contextual data about the given environment 100, and (vii) geolocation data about the body or the given environment 100.

Figure 6:
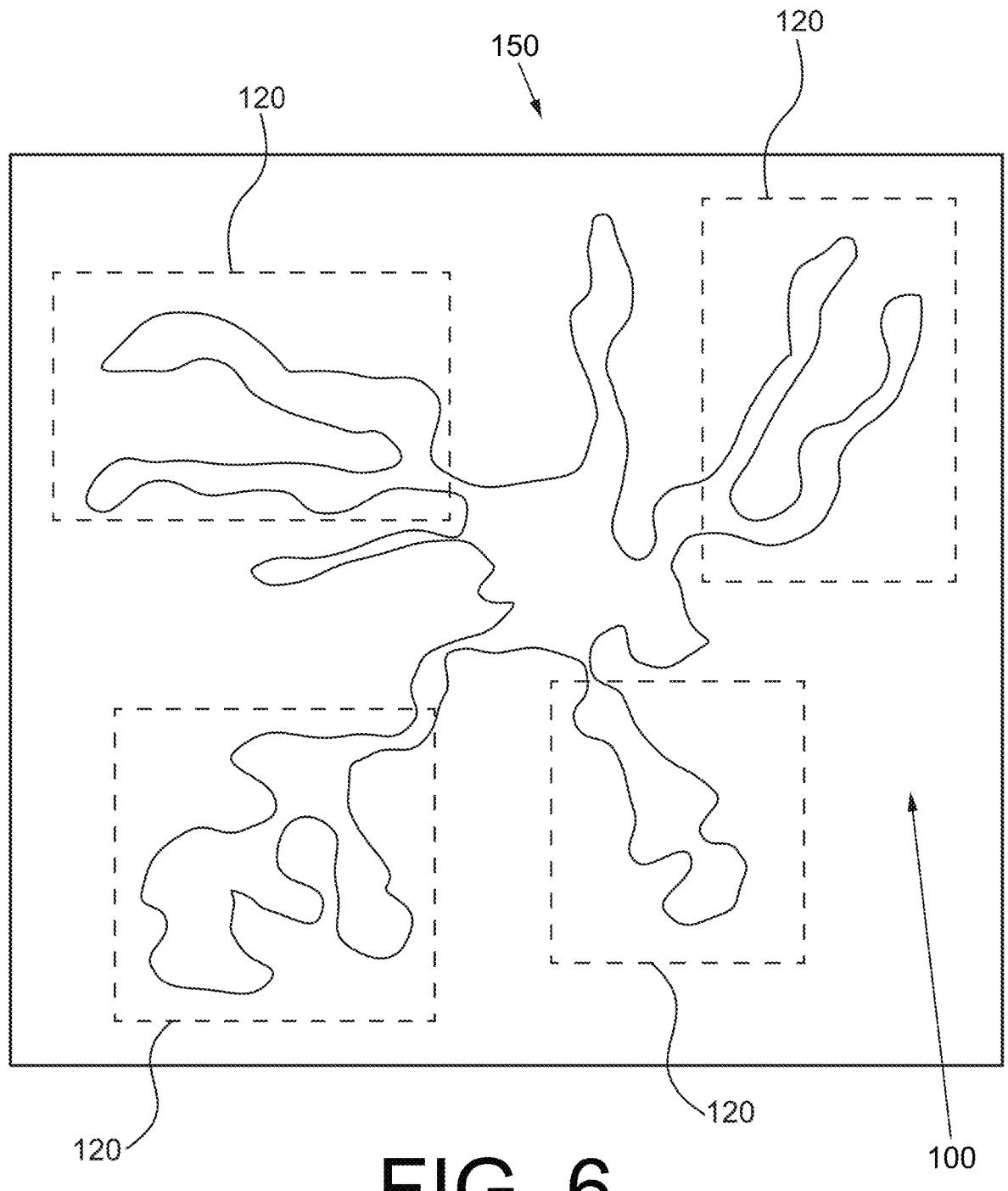
FIG. 6 is an example pattern of movement or trajectory for a body in the given environment.

FIG. 6 shows an example pattern of movement that has been grouped or segmented into the zones 120 as described above. The segmenting can be performed by image processing software, or by a trained MLA.

In certain embodiments, the determining the zones 120 comprises comparing the pattern of movement with a reference pattern of movement of a reference body in a reference environment. In this respect, the method may further comprise selecting the reference pattern of movement and accessing the reference pattern of movement from a database where it is stored, for example.

The reference pattern of movement can define a typical daily living habit of a reference body, as identified by one or more of an age of the reference body, a gender of the reference body, a cultural background of the reference body, a DNA-mapping of the reference body, a biomarker of the reference body, a geolocation of the reference body, a medication of the reference body, a condition of the reference body (e.g. a disease or state), a state of the reference body (e.g. high energy, low energy, normal energy). The daily living habit can be defined as one or more of: (i) a time spent in one or more zones of the reference environment, (ii) a time of day spent in one or more zones of the reference environment, (iii) a sequence of being located in one or more zones of the reference environment, (iv) a frequency of being located in one or more zones of the environment, (v) speed of movement within the environment, (vi) a transition time between one or more zones, and (vi) number of transitions between zones. For example, the reference pattern of movement comprises data considered typical for various age groups including information on how often a person of a particular age moves between a kitchen and a bathroom.

The reference pattern of movement, for the purposes of defining the zones 120 of the environment 100 for the body 160, can be selected based on a relevance of one or more of: (i) an age/gender of the body 160 compared to the reference body, (ii) a condition/diagnosis/state of the body 160 compared to a condition/diagnosis/state of the reference body, (iii) a time of year that the pattern of movement is determined compared to a time of year that the reference pattern of movement was determined, (iv) a geolocation of the body 160 compared to a geolocation of the reference body, (v) a specified event of the body 160 compared to a specified event of the reference body, (vi) gender of the body 160 compared to a gender of the reference body, (vii) cultural background of the body 160 compared to a cultural background of the reference body, (viii) DNA mapping of the body 160 compared to DNA mapping of the reference body, (ix) biomarker of the body 160 compared to a biomarker of the reference body, and (x) medication being taken by the body 160 compared to a medication taken by the reference body.

In one example, if the pattern of movement that is determined for the body 160 indicates that the body 160 moves between one location and another location twenty times in one day, the computer system 200 may determine that one of the locations is a bathroom zone, based on the reference pattern of movement that indicates that a person of the same age as the body 160 visits the bathroom on average ten times a day.

In certain embodiments, the method 500 comprises obtaining physiological data about the body 160 at the time of determining the pattern of movement. The physiological data can include one or more of respiratory rate; heart rate; eyelid motion; limb flailing; limb motion, body positions such as sitting, lying, standing; speech parameters such as intensity, pitch, speed, waveform; facial expressions such as grimace, smile, blank. The physiological data may be determined based on the signals received by the mapping device 210 (e.g. continuous wave RF signal, pulsed RF signal, etc.) and/or data received from the sensor(s) 230.

In certain embodiments, the method 500 comprises obtaining contextual data about the given environment at the time of determining the pattern of movement. The contextual data can include one or more of sound data, air quality data, air humidity data, temperature data, barometric pressure data, oxygen levels, carbon dioxide levels, luminosity levels, UV levels, and vibration data. The contextual data may also include time of day, day of week, season, geolocation and weather conditions. The contextual data may be obtained using one or more of the sensors 230.

In certain embodiments, the method 500 comprises determining the location of inanimate objects in the given environment. This can be performed using RF radar signatures of the inanimate objects. The method 500 may include the processing of the RF radar signals to determine the location of the inanimate objects.

In certain embodiments, the determining the functional identity of the at least one zone 120 comprises mapping any one or more of the physiological data, the contextual data, the location of the inanimate objects, and/or movements corresponding to activities (sleeping, sitting, eating, walking etc.) to determine the functional identity of the at least one zone 120.

The determining the identity of the at least one zone 120 in the given environment 100 may comprise the execution of a Machine Learning Algorithm (MLA). Prior to the obtaining the pattern of movement, the method may further comprise executing a training process for the MLA. In certain embodiments, the training process comprises providing at least one training set, the training set including patterns of movement of reference bodies in reference environments, and a target value representative of a functional identity of a zone; the reference patterns of movement of the reference bodies including at least one of: an age/gender of the reference bodies, a condition/diagnosis of the reference bodies, a time of year that the reference pattern of movement is determined, a geolocation of the reference bodies, specified event(s) of the reference bodies, time spent in one or more zones of the reference environments, time of day spent in one or more zones of the reference environment, a sequence of being located in one or more zones of the reference environment, a frequency of being located in one or more zones of the environment. In certain embodiments, the training set also includes physiological data, the contextual data, the movement data, and the location of the inanimate objects.

In certain embodiments, the method 500 comprises establishing a baseline pattern of movement for the body in the given environment. For example, the baseline pattern of movement can be established by determining an average baseline pattern of movement of the body 160 over a number of days, weeks or months. In other examples, the baseline pattern of movement is not that of the body 160, but that of a reference body having similar characteristics (e.g. gender, age, health condition etc.).

In certain situations, an adjustment to the baseline pattern of movement may be necessary based on known external factors and their effect on the baseline. The external factor may be one or more of a medication being administered to the body 160, a recovery from a recent treatment to the body (e.g. post-operative), a current treatment to the body 160, and the like.

In certain embodiments, if a change is detected in the baseline pattern of movement for the body 160 in the given environment 100 and/or if a change from the baseline pattern of movement is outside of a predetermined threshold, the method 500 comprises triggering an alert.

Examples of changes from baseline pattern of movement comprise one or more of (i) decrease/increase in time spent in one location within a predetermined time period (e.g. increase of time spent in the sleeping zone), (ii) repetitive movement such as pacing back and forth within a predetermined time period, (iii) decrease/increase of time spent in one location within a predetermined time period (e.g. the kitchen), (iv) decrease/increase in frequency of visiting one location within a predetermined time period, (v) a decrease/increase in transition time, (vi) decrease/increase in the number of transitions, (vii) changes in activities conducted in a specific zone, or the like. These can be biomarkers of various medical or psychological conditions including stress.

The method 500 may further comprise determining one or more of an outer boundary of the given environment 100, and an inner boundary 140 of the given environment 100. Determining the outer boundary 110 of the given environment 100 may comprise identifying outermost points of a trajectory of the body 160 in the given environment 100. Determining the inner boundary 140 of the given environment 100 may comprise segmenting a trajectory of the body 160 in the given environment into zones of movement, and approximating a boundary in-between the zones 120.

In certain embodiments, segmenting the trajectory into zones comprises grouping together a plurality of co-ordinates or location vectors of the trajectory of the body based on:
  (i) a physical proximity of the co-ordinates or location vectors to one another,
  (ii) a duration of time spent at certain of the co-ordinates or location vectors by the body in a predetermined time interval,
  (iii) a time(s) of day of location of the body 160 at certain co-ordinates or location vectors in the predetermined time interval,
  (iv) a sequence of location of the body 160 at certain co-ordinates or location vectors in the predetermined time interval,
  (v) a frequency of location of the body 160 at certain co-ordinates or location vectors in the predetermined time interval,
  (vi) contextual data about the given environment 100, and
  (vii) geolocation data about the body/given environment 100.

The segmenting the trajectory can also include taking into consideration additional data, such as contextual data, as described herein.

The determining the one or more of an outer boundary 110 of the given environment 100, and an inner boundary 140 of the given environment 100 may comprise the computer system 200 executing a Machine Learning Algorithm (MLA). Prior to determining the one or more of an outer boundary 110 of the given environment 100, and an inner boundary 140 of the given environment 100, the method 500 may further comprise executing a training process for the MLA.

The training process may comprise providing at least one training set, the training set including a reference trajectories of movement of reference bodies in given environments with outer and inner boundaries, and a target value representative of a location of one or more of an outer boundary and an inner boundary; the reference trajectories of movement optionally including at least one of: an age/gender of the reference bodies, a condition/diagnosis of the reference bodies, a time of year that the reference pattern of movement is determined, a geolocation of the reference bodies, specified event(s) of the reference bodies, time spent in one or more zones of the reference environments, time of day spent in one or more zones of the reference environment, a sequence of being located in one or more zones of the reference environment, a frequency of being located in one or more zones of the environment, transition time between zones, number of transitions between zones. The reference trajectories of movement may describe movement of the bodies from position to position, and/or may describe motion of the bodies while at a stationary position or while moving.

In certain embodiments, the determined identity of the zone 120 may be validated based on a user input. After the system 200 has determined the identities of the zones 120, a validation by the body 160 may be requested by the system 200. For example, the mapping device 210 may include a user interface for the user input. Alternatively, the validation by the body 160 may be provided through another device (not shown) associated with the body 160, and in operative communication with the computer system 220. The device may be the body's watch or cellphone, another portable device, or a non-portable device such as a wall-mounted device, which can be configured to receive and transmit signals to/from the mapping device 210 and/or computer system 220 and to request and receive user input with regards to validating the identity of the zones 120. For example, in certain embodiments, the body 160 would be commanded to go to a particular zone 120 and confirm their presence in that zone 120. In these embodiments, instructions may be sent by the computer system 220 to the body's cellphone to cause the cellphone to display or speak a command to the body 160 such as "Go to the kitchen and press 'confirm'". The confirmation of the body 160 would be received by the computer system 220 and the body's detected location matched with the functional identity of the zone 120. The body 160 may be asked to confirm a type of activity that they are performing. The movement and/or other data corresponding to the activity may then be labeled with the activity and used to train an MLA for identifying activities being performed by the body 160.

Mapping Boundaries

Figure 7:
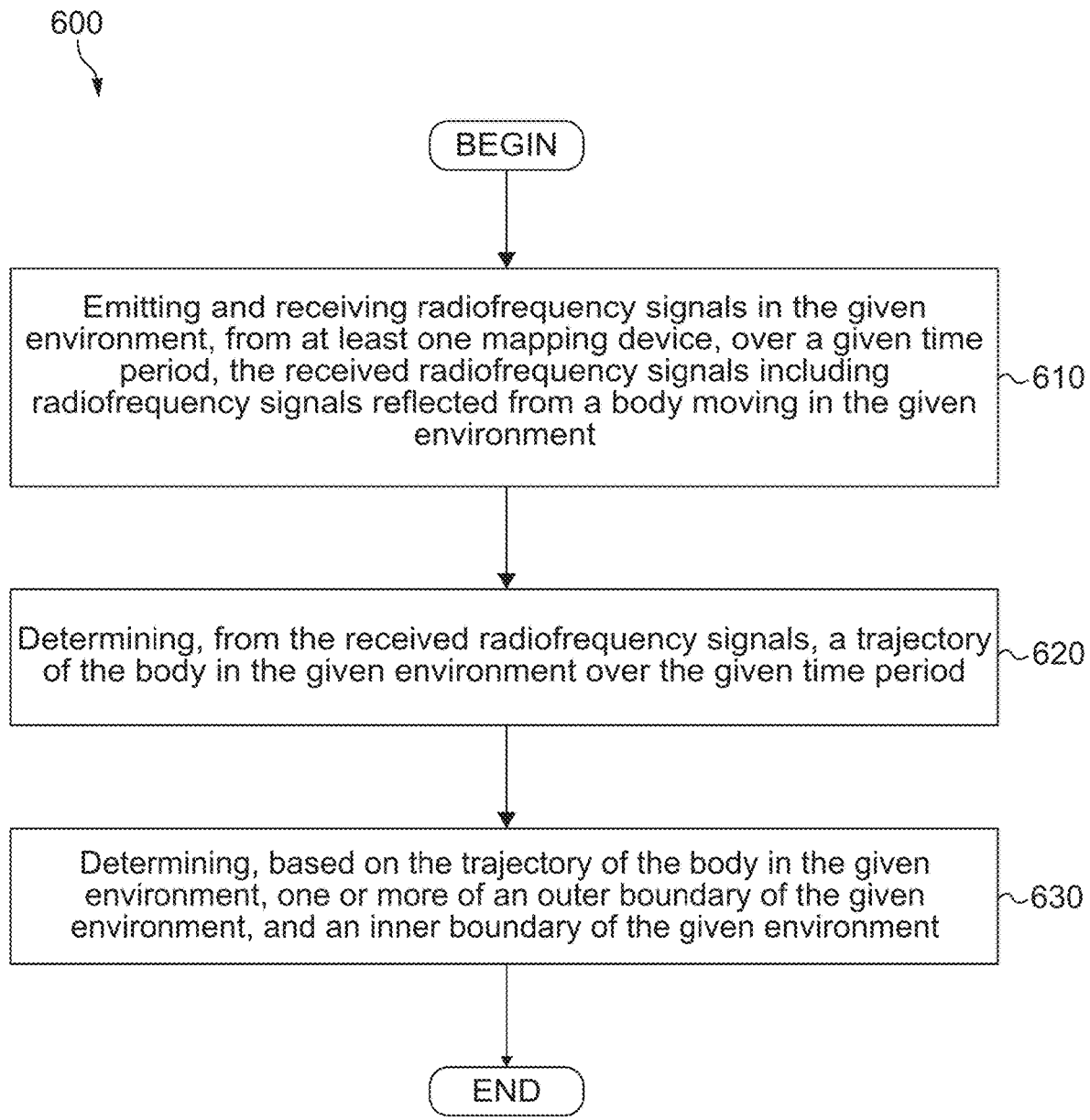
FIG. 7 is a diagram of a method for mapping boundaries of an environment, in accordance with an embodiment of the present technology.

FIG. 7 depicts a method 600 for mapping boundaries of a given environment 100, such as the given environment 100, in accordance with at least one non-limiting embodiment.

At step 610, the method 600 comprises emitting and receiving radio frequency signals in the given environment 100, from at least one mapping device, such as the mapping device 120, over a given time period, the received radio frequency signals including radio frequency signals reflected from a body, such as the body 160, moving in the given environment. Step 610 is optional in method 600.

At step 620, the method 600 comprises determining a trajectory of the body 160 in the given environment 100 over the given time period. In the embodiment of FIG. 7, the trajectory is determined from radio frequency signals.

At step 630, the method 600 comprises determining, based on the trajectory 150 of the body 160 in the given environment 100 over time, an outer boundary 110 and at least one inner boundary 140 of the given environment 100.

Determining the outer boundary 110 may comprises identifying outermost points of the trajectory. For example, in embodiments where the trajectory comprises a plurality of coordinates of the type (x, y), the outermost locations are determined based on identification of coordinates having (max, min) and (min, max).

Determining the inner boundary 140 may comprise segmenting the trajectory into zones of movement, and approximating a boundary 140 in between the zones. In certain embodiments, segmenting the trajectory into zones may comprise grouping a plurality of co-ordinates or location vectors of the trajectory of the body based on: (i) a physical proximity of the co-ordinates or location vectors to one another, (ii) a duration of time spent at certain of the co-ordinates or location vectors by the body in the given time period, iii) a time(s) of day of location of the body at certain co-ordinates or location vectors in the given time period, (iv) a sequence of location of the body at certain co-ordinates or location vectors in the given time period, and (v) a frequency of location of the body at certain co-ordinates or location vectors in the given time period.

The method 600 may further comprise obtaining contextual data about the given environment 100 at the time of determining the trajectory of movement of the body 160. The contextual data may comprise one or more of sound data, air quality data, air humidity data, temperature data, barometric pressure data, oxygen levels, carbon dioxide levels, luminosity levels, UV levels, and vibration data.

In certain embodiments, the method 500 comprises obtaining physiological data about the body 160 at the time of determining the trajectory of movement. The physiological data can include one or more of respiratory rate; heart rate; eyelid motion; limb flailing; body positions such as sitting, lying, standing; speech parameters such as intensity, pitch, speed, waveform; facial expressions such as grimace, smile, blank. The physiological data may be determined based on the signals received by the mapping device 210 (e.g. continuous wave RF signal, pulsed RF signal, etc.) and/or data received from the sensor(s) 230.

The method 600 may further comprise determining the location of inanimate objects in the given environment 100. This can be performed using the RF radar signature described earlier. This can be performed using RF radar signatures of the inanimate objects. The method 500 may include the processing of the RF radar signals to determine the location of the inanimate objects.

In certain embodiments, determining the outer or inner boundary comprises mapping any one or more of the physiological data, the contextual data and the location of the inanimate objects to the trajectory.

In certain embodiments, the determining one or more of the outer boundary 110 of the given environment 100, and the inner boundary 140 of the given environment 100 comprises the computer system executing a Machine Learning Algorithm (MLA). The method may further comprise executing a training process for the MLA prior to determining the one or more of an outer boundary 110 of the given environment 100, and an inner boundary 140 of the given environment 100.

The training process may comprise providing at least one training set, the training set including a reference trajectories of movement of reference bodies in given environments with outer and inner boundaries, and a target value representative of a location of one or more of an outer boundary and an inner boundary; the reference trajectories of movement optionally including at least one of: an age/gender of the reference bodies, a condition/diagnosis of the reference bodies, a time of year that the reference pattern of movement is determined, a geolocation of the reference bodies, specified event(s) of the reference bodies, time spent in one or more zones of the reference environments, time of day spent in one or more zones of the reference environment, a sequence of being located in one or more zones 120 of the reference environment, a frequency of being located in one or more zones of the environment, transition time between zones 120, number of transitions, environment conditions (rain, snow, heat etc).

In certain embodiments, the method 600 comprises one or more of the steps of the method 500 for determining a pattern of movement of the body and a functional identity of at least one zone in the given environment based on the pattern of movement of the body.

Monitoring/Tracking Body

There is also provided a method for monitoring a body in a given environment, such as the body 160 in the environment 100. The environment 100 may have been mapped according to embodiments of method 500 and/or method 600, or in any other way. In certain embodiments, the environment 100 is mapped by method 600 followed by method 500. The mapped outer/inner boundaries can facilitate identification of the functional identity of at least one zone. In certain embodiments, the method for monitoring the body 160 comprises detecting changes in one or more of (i) the pattern of movement of the body 160 in the given environment 100, (ii) the trajectory of the body 160 in the given environment 100, (iii) the speed of movement of the body 160 in the given environment, (iv) the type of movement of the body 160 in the given environment (e.g. motion associated with falls, range of motion which could be useful during rehabilitation), (v) physiological data about the body 160 in the given environment, and (vi) contextual data about the environment 100. The type of body movement can include posture, such as slouching or upright, position such as lying or standing, changes such as the ones seen in some type of falls and other events like fainting, falling asleep, tripping, and the like.

In certain embodiments, at least one or more of the above monitored characteristics can provide information about a quality of sleep of the body 160, a commencement of a health condition or disease of the body 160, a progression of a health condition or disease in the body 160, a state of mind of the body 160, an activity of the body 160, and a reaction of the body to a medication or other treatment.

Tracking a Person

Figure 8:
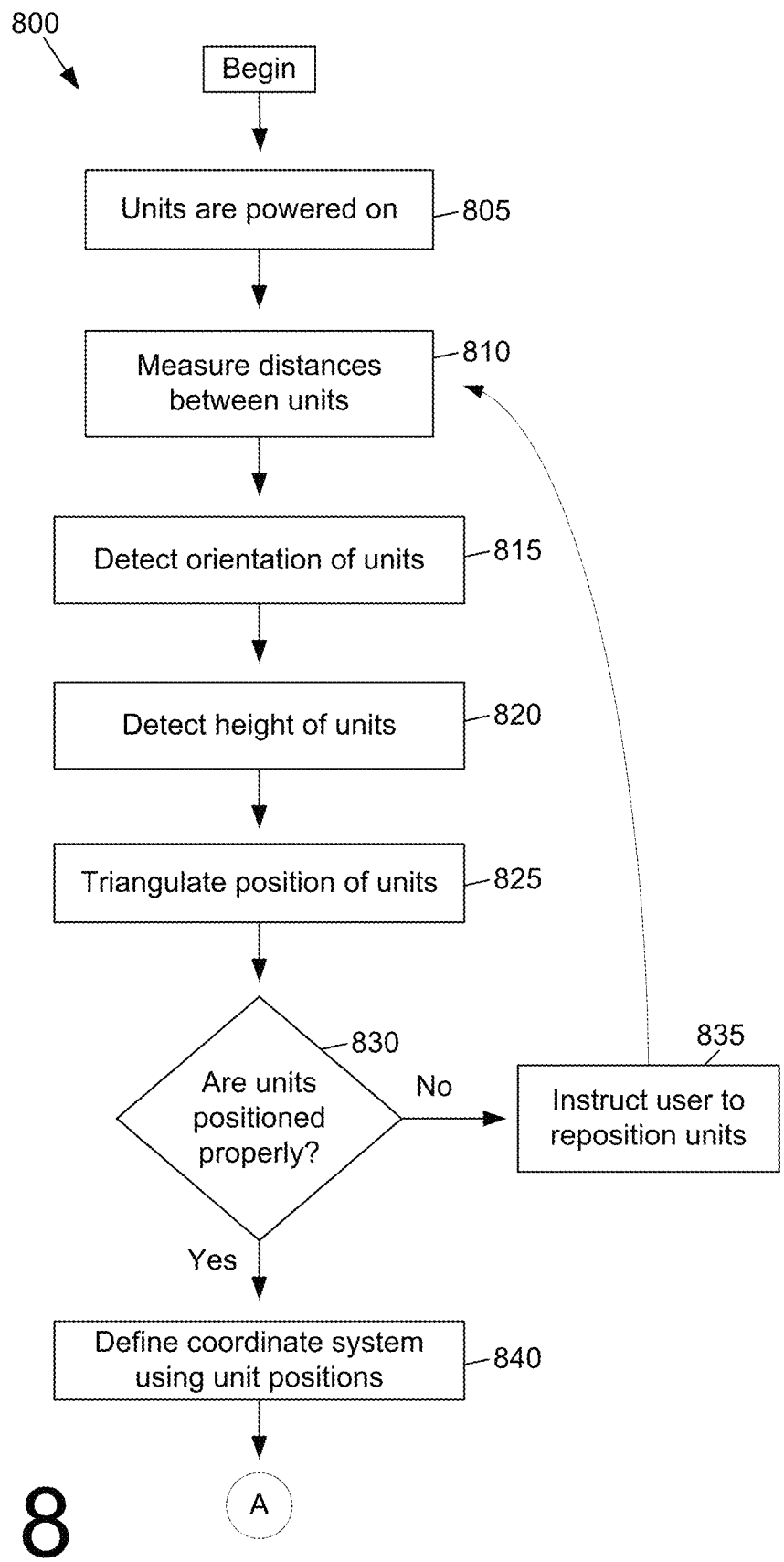
FIGS. 8 and 9 are a diagram of a method for tracking a person, in accordance with an embodiment of the present technology.
Figure 9:
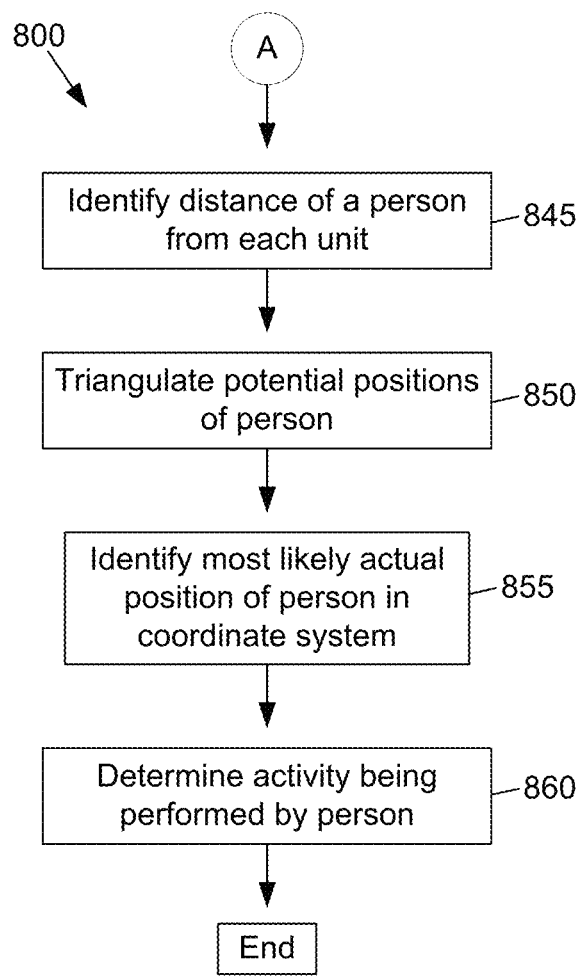

FIGS. 8 and 9 depict a method 800 for tracking a person using the mapping device 210, in accordance with at least one non-limiting embodiment.

At step 805 the units 212, 213, and 214 of the mapping device 210 may be powered on. The units 212, 213, and 214 may be connected to, or plugged into, wall sockets. As described above, the mapping device 210 may have any number of units 212, 213, and 214. The number of units 212, 213, and 214 to be used may be determined by the size, number of rooms, and/or number of floors that the mapping device 210 is intended to monitor. The number of units 212, 213, and 214 to be used may be determined based on the desired function, or a desired accuracy, of the mapping device 210. Increasing the number of units 212, 213, and 214 may increase the accuracy of the tracking and/or other determinations performed by the mapping device 210.

At step 810 the distances between each of the units 212, 213, and 214 may be determined. Any suitable technique may be used to determine the distances between the units 212, 213, and 214. As described above, the units 212, 213, and 214 may measure the time of flight of signals, such as UWB signals, sent between the units 212, 213, and 214 and use that time of flight to determine the distances between each of the units 212, 213, and 214. The time of flight may be measured using RF signals, acoustic signals, and/or other types of signals. The main unit 212, the unit 213, the unit 214, and/or the computer system 220 may calculate and/or store the distances between each of the units 212, 213, and 214. A distance between units 212 and 213 may be determined, a distance between units 212 and 214 may be determined, and/or a distance between units 213 and 214 may be determined.

At step 815 the orientation of each of the units 212, 213, and 214 may be determined. The units 212, 213, and 214 may include a magnetometer, and/or any other suitable sensor, for determining the orientation of the units 212, 213, and 214. The orientation of each unit 212, 213, and 214 may be determined and stored by each of the respective units 212, 213, and 214. The orientation may be transmitted to and stored by the main unit 212, the unit 213, the unit 214, and/or the computer system 220.

At step 820 the height of each of the units 212, 213, and 214 may be determined. Each unit may include a barometric sensor, and/or any other suitable sensor, for determining the height of each unit 212, 213, and 214. The units 212, 213, and 214 may determine whether they are on a same floor as each other, or whether they are on different floors. The units 212, 213, and 214 may determine a height of each unit above the floor. The height of each unit 212, 213, and 214 may be determined and stored by each of the respective units 212, 213, and 214. The height may be transmitted to and stored by the main unit 212, the unit 213, the unit 214, and/or the computer system 220.

At step 825 the position of each of the units may be triangulated. The positions may be triangulated using the distances determined at step 820. If three units 212, 213, and 214 are in use, a triangle may be defined with each of the units 212, 213, and 214 at one of the vertices of the triangle. The position of each of the units 212, 213, and 214 may be triangulated by the units 212, 213, and 214 themselves and/or the computer system 220.

At step 830 a determination may be made as to whether the units are positioned properly. The determination may be made by the main unit 212, the unit 213, the unit 214, and/or the computer system 220. Based on the height of units determined at step 820, a determination may be made that the units 212, 213, and 214 have been placed on different floors of the environment 100. If the units 212, 213, and 214 were placed on different floors, a determination may be made that the units are not positioned properly and should be repositioned.

The distances between units 212, 213, and 214 determined at step 810, the orientation of units 212, 213, and 214 determined at step 815, and/or the triangulated positions of units 212, 213, and 214 determined at step 825 may be used to determine whether the units 212, 213, and 214 are properly positioned. If the units are too far apart and/or not oriented correctly such that the RF signals between the units 212, 213, and 214 do not sufficiently intersect, a determination may be made that the units are not positioned properly and should be repositioned.

If the units are determined to be positioned incorrectly, at step 835 an operator may be instructed to reposition one or more of the units 212, 213, and 214. The operator may be using a computing environment 400, such as a smartphone, while configuring the mapping device 210, and a notification may be provided on the computing environment 400 instructing the user that the units 212, 213, and 214 should be repositioned. After the user has repositioned the units, the method 800 may proceed from step 835 to 810, where the distances will be measured between the repositioned units.

The notification at step 835 may indicate which of the units 212, 213, and 214 should be repositioned. The notification may indicate how the units 212, 213, and 214 should be repositioned. In one example the user may be notified that the units 212, 213, and 214 are on different floors and should be placed on the same floor. In another example the user may be notified that the units 212, 213, and 214 are too far apart from each other, and either should be moved, or additional units 212, 213, and 214 should be added to the mapping device 210. In yet another example the user may be notified that the units 212, 213, and 214 should be reoriented, such as if one of the units is facing an outside wall of the environment 100 rather than towards the interior of the environment 100.

After a determination has been made at step 830 that the units are positioned properly, the method may proceed to step 840. At step 840 a coordinate system may be defined using the positions of units determined at step 825. The coordinate system may be a two-dimensional coordinate system with an x and y axis. The coordinate system may be multiple two-dimensional coordinate systems, such as one coordinate system for each floor. The coordinate system may be a three-dimensional coordinate system. Each of the units 212, 213, and 214 may be assigned a position within the coordinate system. The location of the units 212, 213, and 214 within the coordinate system may be stored in a database, such as a database stored on and/or managed by the computer system 220.

At step 845 the distance between a person and each of the units 212, 213, and 214 may be determined. The person may be moving or stationary. The distance between each of the units 212, 213, and 214 and the person may be determined, as described above, by transmitting and receiving RF signals. The reflected RF signals may indicate, for each of the units 212, 213, and 214, the distance between the respective unit 212, 213, and 214 and the person. A peak having a threshold amplitude may be identified in the reflected RF data received by each of the units 212, 213, and 214. That peak may correspond to the person.

The distances may be determined by the main unit 212, the unit 213, the unit 214, and/or the computer system 220. The distances may be determined by each individual unit 212, 213, and 214 and then transmitted to the computer system 220. A subset of the units 212, 213, and 214 may detect the person. As the person moves around the environment 100, the units 212, 213, and 214 may gain or lose tracking of the person. The potential positions of the person may be determined based in part on a last known position of the person and/or a direction of movement of the person. If the person's position cannot be triangulated at a specific point in time, such as because only two of the units 212, 213, and 214 are detecting the person, the position of the person may be inferred based on any distances that were detected, last known position of the person, and/or movement data of the person such as direction, speed, etc.

At step 850 the distances determined at step 845 may be used to triangulate potential positions of the person. The potential positions may be calculated by the computer system 220. The potential positions may be calculated based on the distances measured at step 845 and/or based on the positions of each of the units 212, 213, and 214 in the coordinate system defined at step 840. The potential positions may be coordinate pairs within the coordinate system.

At step 855 one of the potential positions determined at step 850 may be selected as the most likely position of the person. Various factors may be used for selecting the most likely position, such as last known position of the person, movement data of the person, location of various fixed objects in the environment 100 such as furniture and/or walls, etc. The data from each of the individual units 212, 213, and 214, such as distance of each unit 212, 213, and 214 from the person, may be weighted based on how reliable the data from the individual unit 212, 213, and 214. For example if the RF data from unit 213 has a lot of noise, when determining the position of the person the RF data from that unit 213 may be weighted lower than the RF data from the units 212 and 214.

At step 860 the activity being performed by the person may be identified. The activity may be determined based on a function of the room in the environment 100 that the person is in. The activity may be determined based on a radar signature of the person. A machine learning algorithm (MLA) may be used to predict the activity that the person is performing based on the radar signature of that person. Various sensors in the units 212, 213, and 214 may be used to determine the activity that the person is performing. For example if a temperature sensor detects that temperature is going up, a humidity sensor detects that humidity is increasing, and/or the position of the person determined at step 855 indicates that the person is in the bathroom, a determination may be made that the person is showering. As described above, if a deviation from a normal pattern is detected, such as if the person has fallen and/or isn't moving, an alert may be transmitted.

While the above-described implementations have been described and shown with reference to particular steps performed in a particular order, it will be understood that these steps may be combined, sub-divided, or re-ordered without departing from the teachings of the present technology. At least some of the steps may be executed in parallel or in series. Accordingly, the order and grouping of the steps is not a limitation of the present technology.

It should be expressly understood that not all technical effects mentioned herein need to be enjoyed in each and every embodiment of the present technology.

Modifications and improvements to the above-described implementations of the present technology may become apparent to those skilled in the art. The foregoing description is intended to be exemplary rather than limiting. The scope of the present technology is therefore intended to be limited solely by the scope of the appended claims.

The invention claimed is:

1. A method of mapping a given environment, the method executable by a processor of a computer system, the method comprising:
receiving radio frequency (RF) signals over a period of time;
determining, based on the RF signals, a trajectory of a body in the given environment;
determining segments of the trajectory corresponding to a zone in the given environment by grouping a plurality of coordinates or location vectors of the trajectory based on:
a physical proximity of the plurality of coordinates or location vectors to one another,
a duration of time spent at each of the plurality of coordinates or location vectors by the body in the period of time,
a time of day during which the body is located at each of the plurality of coordinates or location vectors in the period of time,
a sequence in which the body is located at each of the plurality of coordinates or location vectors in the period of time, or
how frequently the body is located at each of the plurality of coordinates or location vectors in the period of time;
determining, based on the segments, an outer boundary of the zone in the given environment and an inner boundary of the zone in the given environment;
determining, based on the RF signals, a pattern of movement of the body in the given environment; and
determining, based on the pattern of movement of the body in the given environment, a functional identity of the zone in the given environment.

2. The method of claim 1, further comprising emitting the RF signals in the given environment, from at least one mapping device, over the period of time, the received RF signals including RF signals reflected from the body moving in the given environment.

3. The method of claim 2, further comprising receiving, by the at least one mapping device, sound data, and wherein determining the trajectory of the body in the given environment comprises determining the trajectory of the body in the given environment based on the received RF signals and the sound data.

4. The method of claim 1, wherein determining the trajectory of the body in the given environment comprises determining the trajectory based on a first subset of the received RF signals, and wherein determining the pattern of movement comprises determining the pattern of movement based on a second subset of the received RF signals.

5. The method of claim 1, further comprising determining, based on the received RF signals, physiological data about the body during the period of time.

6. The method of claim 1, further comprising:
tracking the body in the given environment;
detecting, based on the tracking, a deviation from the pattern of movement; and
after detecting the deviation, transmitting an alert indicating the deviation.

7. The method of claim 1, further comprising:
tracking the body in the given environment;
determining, based on the tracking and the received RF signals, that the body has fallen; and
transmitting an alert indicating that a fall has been detected.

8. The method of claim 1, further comprising comparing the pattern of movement with a reference pattern of movement of a reference body in a reference environment.

9. The method of claim 8, wherein the reference pattern of movement is selected based on (i) an age/gender of the body compared to the reference body, (ii) a condition/diagnosis of the body compared to a condition/diagnosis of the reference body, (iii) a time of year that the pattern of movement is determined compared to a time of year that the reference pattern of movement was determined, (iv) a geolocation of the body compared to a geolocation of the reference body, (v) a specified event of the body compared to a specified event of the reference body, (vi) a gender of the body compared to a gender of the reference body, (vii) cultural background of the body compared to a cultural background of the reference body, (viii) DNA mapping of the body compared to DNA mapping of the reference body, (ix) a biomarker of the body compared to a biomarker of the reference body, (x) a medication being taken by the body compared to a medication taken by the reference body, (xi) contextual data about the given environment, (xii) a specific activity of the body compared to a specific activity of the reference body, or (xiii) prior patterns of movement in the given environment compared to the reference pattern of movement.

10. The method of claim 8, wherein the reference pattern of movement defines one or more of: (i) a time spent in one or more zones of the reference environment, (ii) a time of day spent in one or more zones of the reference environment, (iii) a sequence of being located in one or more zones of the reference environment, (iv) a frequency of being located in one or more zones of the reference environment, (v) a speed of movement within the reference environment, (vi) a transition time between one or more zones of the reference environment, (vii) number of transitions between zones of the reference environment, and (viii) one or more activities performed in zones of the reference environment.

11. The method of claim 1, wherein determining the pattern of movement comprises determining an average pattern of movement based on a plurality of patterns of movement of the body determined in a plurality of different time slots.

12. The method of claim 1, further comprising:
receiving, by a device comprising a plurality of microphones, sound data corresponding to the body; and
determining, based on the sound data, a direction of the body in relation to the device.

13. A system for mapping boundaries of a given environment, the system comprising a computer system in communication with one or more mapping devices configured to emit and receive radio frequency signals, the computer system comprising at least one processor and memory storing a plurality of executable instructions which, when executed by the at least one processor, cause the system to:
determine, based on the received radio frequency signals, a trajectory of a body in the given environment over a period of time;
determine segments of the trajectory by grouping a plurality of coordinates or location vectors of the trajectory based on:
a physical proximity of the plurality of coordinates or location vectors to one another,
a duration of time spent at each of the plurality of coordinates or location vectors by the body in the period of time,
a time of day during which the body is located at each of the plurality of coordinates or location vectors in the period of time,
a sequence in which the body is located at each of the plurality of coordinates or location vectors in the period of time, or
how frequently the body is located at each of the plurality of coordinates or location vectors in the period of time; and
determine, based on the segments, one or more outer boundaries of the given environment and one or more inner boundaries of the given environment.

14. The system of claim 13, wherein the one or more mapping devices comprise one or more microphones, and wherein the instructions, when executed by the at least one processor, cause the system to:
receive sound data captured by the one or more microphones; and
determine, based on the sound data, the trajectory.

15. The system of claim 13, wherein the instructions that cause the system to determine the one or more inner boundaries of the given environment comprise instructions that cause the system to approximate a boundary in between zones of movement.

16. A method for mapping a given environment, the method executable by a processor of a computer system, the method comprising:
emitting, by at least one mapping device, radio frequency (RF) signals in the given environment;
receiving, by the at least one mapping device, reflected RF signals that were reflected from a body in the given environment;
receiving, by one or more microphones of the at least one mapping device, sound data;
determining, based on the reflected RF signals, a pattern of movement of the body in the given environment; and
determining, based on the sound data and the pattern of movement of the body in the given environment, a functional identity of a zone in the given environment.

17. The method of claim 16, further comprising:
determining a baseline pattern of movement for the body in the given environment;
detecting a change in the baseline pattern of movement for the body in the given environment; and
after determining that the change in the baseline pattern of movement is outside of a predetermined threshold, triggering an alert.

18. The method of claim 16, wherein the pattern of movement indicates motions of the body that occur while the body remains at a position in the given environment.

19. The method of claim 16, wherein determining the pattern of movement of the body in the given environment comprises determining, based on the sound data from the one or more microphones, a direction of a source of the sound data.

20. The method of claim 16, wherein determining the pattern of movement of the body in the given environment comprises determining the pattern of movement of the body based at least in part on the sound data.

* * * * *